United States Patent [19]

Harms

[11] Patent Number: 5,138,054
[45] Date of Patent: Aug. 11, 1992

[54] REACTIVE DYESTUFFS

[75] Inventor: Wolfgang Harms, Odenthal, Fed. Rep. of Germany

[73] Assignee: Bayer Aktiengesellschaft, Leverkusen, Fed. Rep. of Germany

[21] Appl. No.: 657,252

[22] Filed: Feb. 15, 1991

Related U.S. Application Data

[63] Continuation of Ser. No. 499,879, Mar. 27, 1990, abandoned, which is a continuation of Ser. No. 386,934, Jul. 28, 1989, abandoned.

Foreign Application Priority Data

Aug. 13, 1988 [DE] Fed. Rep. of Germany ....... 3827530

[51] Int. Cl.$^5$ ............................................. C07D 498/00
[52] U.S. Cl. ........................................ 544/76; 544/74; 544/75; 564/305
[58] Field of Search ........................ 544/75, 76, 74, 99, 544/102; 564/305

References Cited

U.S. PATENT DOCUMENTS 4,629,788 12/1986 Jager ..................... 544/75

FOREIGN PATENT DOCUMENTS 3344253 4/1985 European Pat. Off. ............ 544/75

*Primary Examiner*—Jose G. Dees
*Assistant Examiner*—D. D. Carr
*Attorney, Agent, or Firm*—Sprung, Horn, Kramer & Woods

[57] ABSTRACT

Triphendioxazine reactive dyestuffs of the general formula

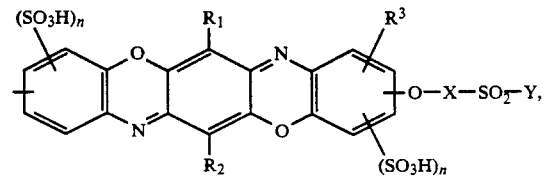

with the substituent definition given in the description, are outstandingly suitable for dyeing and printing materials containing hydroxyl groups or amide groups. They give red dyeings with high wet- and light-fastnesses.

7 Claims, No Drawings

REACTIVE DYESTUFFS

This application is a continuation of application Ser. No. 499,879, filed Mar. 27, 1990, now abandoned, which is a continuation of application Ser. No. 386,934, filed Jul. 28, 1989, now abandoned.

The present invention relates to new triphendioxazine reactive dyestuffs of the general formula $$Y-SO_2-X-O-\qquad\qquad (I)$$

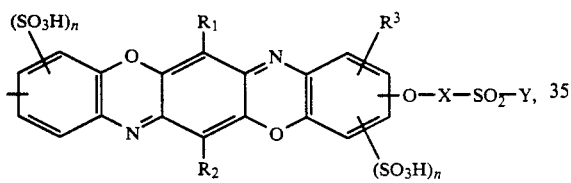

wherein
- X denotes an aliphatic bridge member,
- denotes —CH=CH$_2$ or —CH$_2$—CH$_2$—Z, wherein
- Z denotes a group which can be split off, such as OSO$_3$H, S$_2$O$_3$H, Cl, Br, O—COCH$_3$, OPO$_3$H$_2$ or N(R$_4$)$_3$, where R$_4$=C$_1$-C$_4$-alkyl, but is preferably OSO$_3$H,
- n denotes 0–2, preferably 1,
- R$_1$ and R$_2$ denote H, halogen, C$_1$-C$_4$-alkoxy, optionally substituted phenoxy or aryl, acylamino, carboxyl or carbalkoxy, preferably Cl, and
- denotes H, C$_1$-C$_4$-alkyl, C$_1$-C$_4$-alkoxy, halogen or carboxyl.

Examples of aliphatic bridge members X are straight-chain or branched C$_2$-C$_8$-alkylene radicals which are optionally substituted or interrupted by hetero atoms or O or N or groups containing such atoms, such as ethylene, 1,3- or 1,2-propylene, 1,4-, 1,3- or 2,3-butylene, 1,5-pentylene, 1,6-hexylene, 2,2-dimethyl-1,3-propylene, 2-ethyl-1,3-propylene, 1,4-, 1,3-cyclohexylene, 2-hydroxy-1,3-propylene, 2-oxo-1,3-propylene, 2-sulphato-1,3-propylene, —CH$_2$—CH$_2$O—CH$_2$—CH$_2$—, —(CH$_2$—CH$_2$—O)$_{2-3}$—CH$_2$—CH$_2$—,

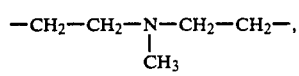

—CH$_2$—CH$_2$—NH—CH$_2$—CH$_2$—,

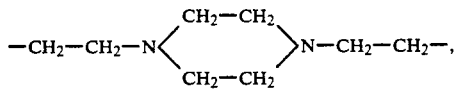

—CH$_2$—CH$_2$—CO—NH—CH$_2$—CH$_2$—, —CH$_2$—CO—NH—CH$_2$—CH$_2$—, —CH$_2$—CH$_2$—NH—CO—CH$_2$—, —CH$_2$—CH$_2$—NH—CO—CH$_2$—CH$_2$—.

Preferred dyestuffs of the formula (I) are those of the formula

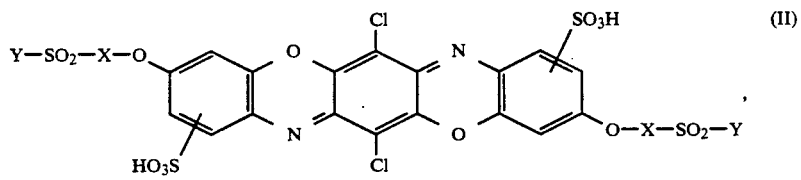

in particular those of the formula

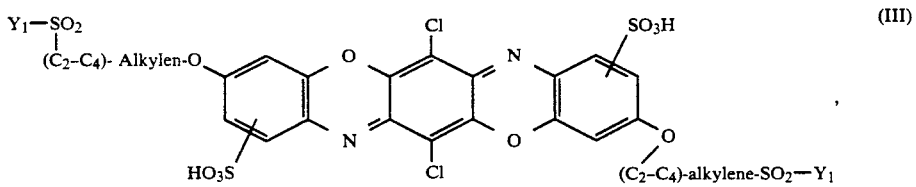

wherein
Y$_1$ denotes CH$_2$—CH$_2$—OSO$_3$H or —CH=CH$_2$.

Quite generally, sulpho groups present in the triphendioxazine ring system are preferably in the o-position relative to the radical —O—X—SO$_2$—Y.

The dyestuffs of the formula (I) are prepared by condensation of ω-(aminophenoxy)-alkyl-β′-hydroxy- or β′-sulphatoethyl sulphones of the formulae

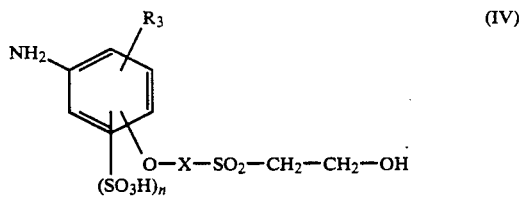

or

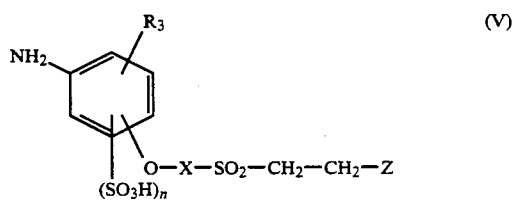

wherein
Z, X, R$_3$ and n have the abovementioned meaning and n 0, 1 or 2,
with 1,4-benzoquinones of the formula

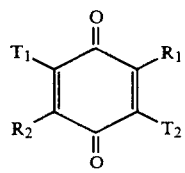

(VI)

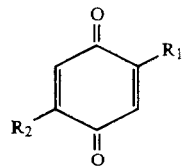

(VIII)

wherein
T$_1$ and T$_2$ hydrogen, Cl, Br, O-(C$_1$-C$_4$)-alkyl or optionally substituted O-phenyl (substituents are in particular Cl, nitro and C$_1$-C$_4$-alkyl) to give compounds of the formula wherein
R$_1$ and R$_2$ have the abovementioned meaning, and oxidation of the adducts primarily formed.

The cyclization of the quinone condensation products (VII) to give the dioxazines (I) can be carried out

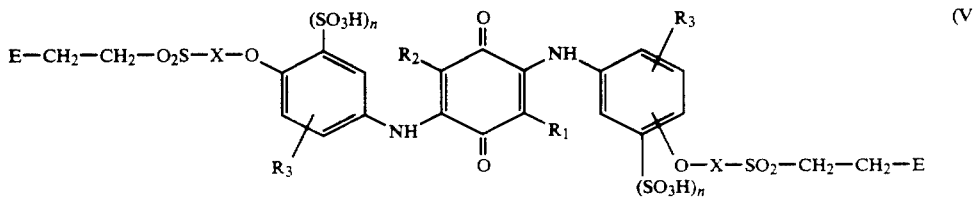

(V)

wherein
E=OH or Z and
Z, R$_1$, R$_2$, R$_3$, X and n have the abovementioned meaning,
and subsequent cyclization of the dianilides (VII) to give the triphendioxazine compounds of the formula (I). In the course of this last operation, sulphato groups and if appropriate sulphonic acid groups or other sulphonic acid groups can be introduced in the customary manner. If appropriate, functional modifications of the —CH$_2$—CH$_2$—OSO$_3$H groups into, for example, —CH=CH$_2$ OR —CH$_2$—CH$_2$—S$_2$O$_3$H groups can then also be carried out.

Depending on the reaction conditions used during the cyclization, the sulphonic acid groups in the benzene rings of the dioxazines (I) can occur either in the o- or in the p-positions relative to the ring oxygen atoms of the dioxazine system.

The condensation of the benzoquinones of the formula (VI) with the amines (IV) or (V) is preferably carried out in an aqueous or aqueous-organic medium with the addition of alkaline condensing agents at pH values of 3-11, preferably 4-8, and temperatures of 20°-90° C., preferably 40°-70° C., or in buffered solutions containing the above alkaline condensing agents. It is also possible to carry out the reaction in a purely organic medium with the addition of acid-binding agents.

Examples of alkaline condensing agents are sodium bicarbonate, sodium carbonate, sodium acetate, potassium acetate, sodium hydroxide solution, potassium hydroxide solution, sodium phosphates and sodium borate. The condensation products of the formula (VII) in general precipitate as sparingly soluble pale brown products.

One variant for the preparation of compounds of the formula (VII) comprises addition of amines (IV) or (V) onto 1,4-benzoquinones of the formula by methods which are known per se, such as are described in German Offenlegungsschriften (German Published Specifications) 2,122,262, 2,124,080, 2,302,383, 2,344,781, 2,503,611 and 2,823,828 and in British Patent Specification 2,019,872, in particular in concentrated sulphuric acid and above all in oleum having SO$_3$ contents of 1-50%, at temperatures of 10°-80° C., if appropriate with the addition of oxidizing agents, such as potassium peroxydisulphate, ammonium peroxydisulphate, manganese dioxide or organic peroxides, or with iodine or iodine-donating agents, such as potassium iodide.

Amines of the formula (IV) and (V) are new and the invention also relates to these. They can be prepared, for example, as follows:

Nitro compounds or acylamino compounds of the formula

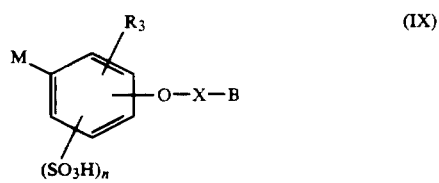

(IX)

wherein
M NO$_2$, acylamino, in particular C$_1$-C$_4$-alkylcarbonylamino, optionally substituted phenylcarbonylamino or carboxy-C$_2$-C$_4$-carbonylamino and
B halogen, in particular Cl or Br, —OSO$_2$-aryl (preferably phenyl or C$_1$-C$_4$-alkylphenyl) or —OSO$_2$—C$_1$-C$_4$-alkyl,
are reacted with 2-mercaptoethanol in a manner which is known per se to give sulphides of the formula

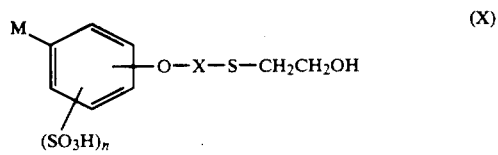

(X)

and these are oxidized in a known manner, for example with H$_2$O$_2$ or chlorine, to give sulphones of the formula

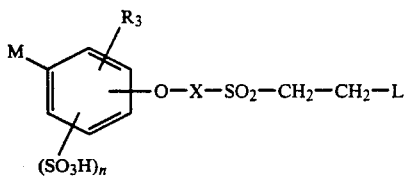 (XI)

wherein
L=OH or Cl,
and the nitro group M is then reduced to the amino group or the acylamino group M is then hydrolyzed, and if. appropriate the OH group L is subsequently converted into a group —OSO$_2$H, —S$_2$O$_3$H or —OPO$_3$H$_2$ and/or sulpho groups are subsequently introduced into the benzene ring (in a known manner with sulphuric acid, oleum, sulphur trioxide or chlorosulphonic acid).

Another specific method for the preparation of compounds of the formula (X) where X=—CH$_2$CH$_2$— comprises one-sided reaction of 2,2'-bis-(hyroxyethyl) sulphide with nitrohalogen compounds of the formula

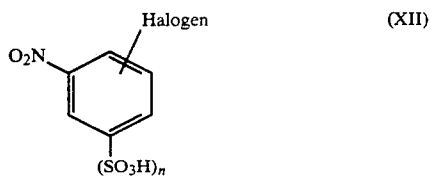 (XII)

wherein
Halogen F, Cl or Br and
n has the abovementioned meaning.

The present invention also relates to the new compounds of the formula

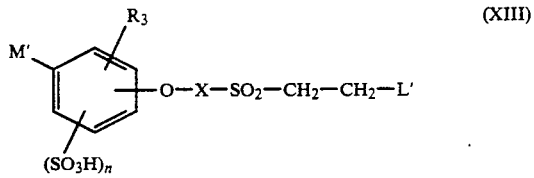 (XIII)

wherein
M' nitro, acylamino or NH$_2$,
L' OH or a group which can be split off anionically, for example —OSO$_3$H, —S$_2$O$_3$H, —OPO$_3$H$_2$ or Cl,
R$_3$ H, C$_1$-C$_4$-alkyl, C$_1$-C$_4$-alkoxy, halogen (Cl or Br) or carboxyl,
X an aliphatic bridge member and
n 0, 1 or 2.
If M' is NO$_2$, n is preferably 0.
Suitable amino compounds of the formulae (IV) and (V) for reaction with the quinones (VI) or (VIII) are, for example:

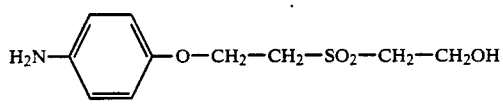

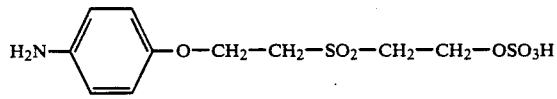

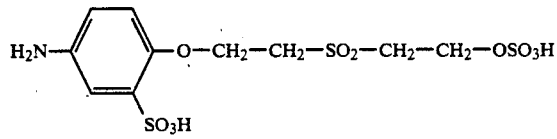

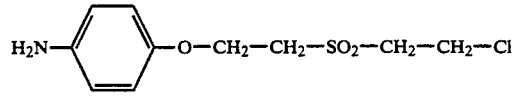

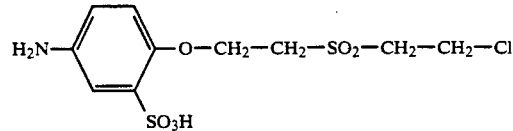

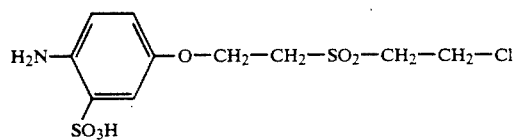
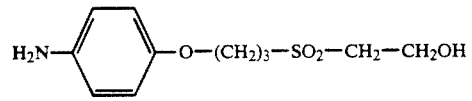
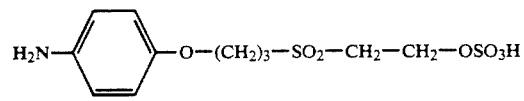
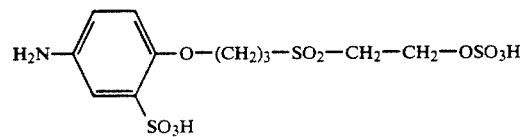
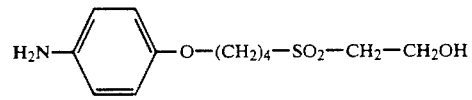
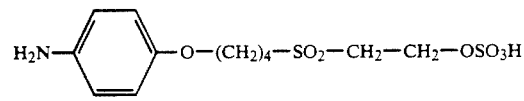
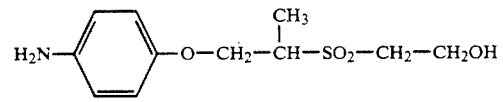
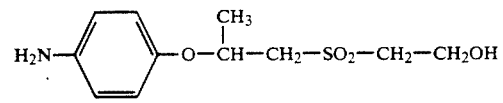
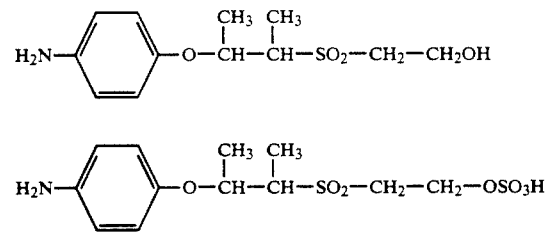
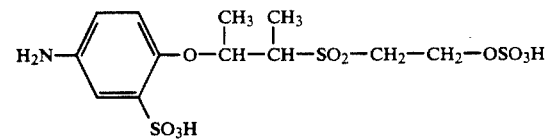
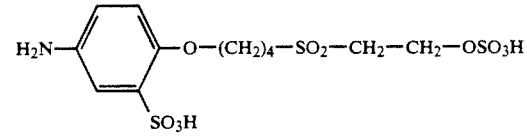

-continued
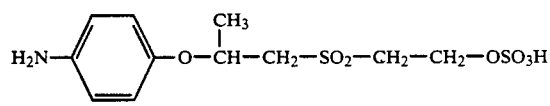
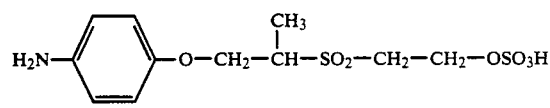
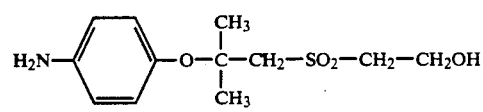
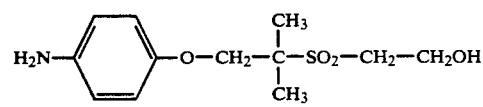
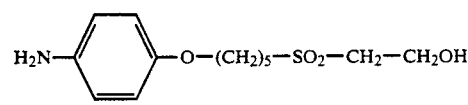
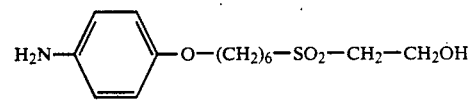
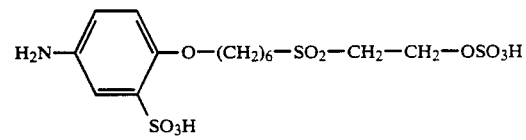
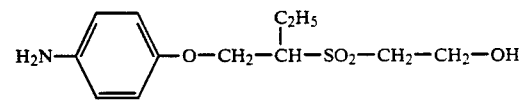
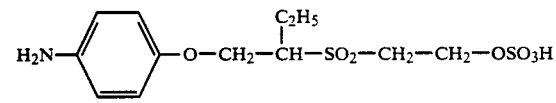
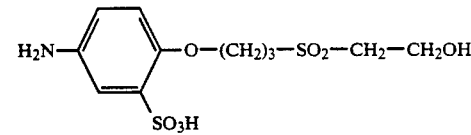
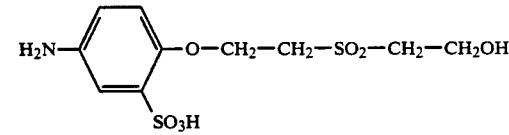
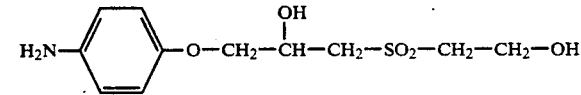
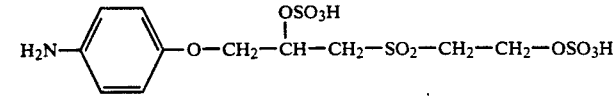

-continued
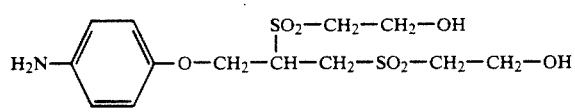
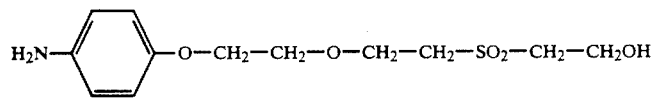
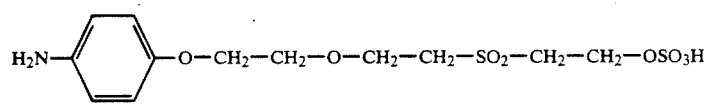
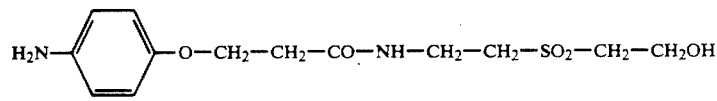
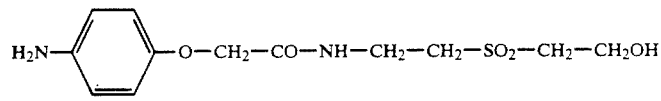
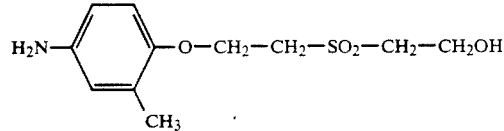
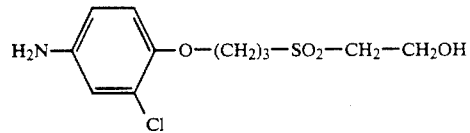
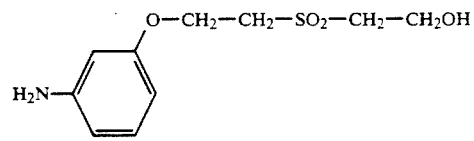
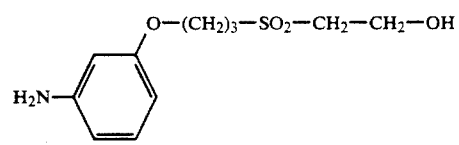
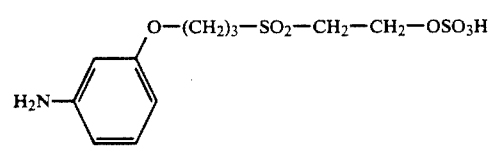
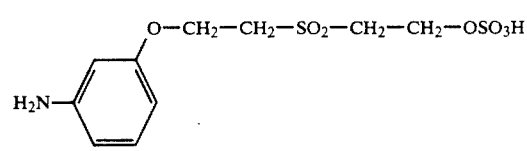

-continued
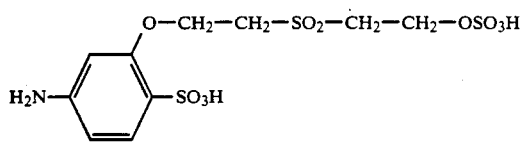
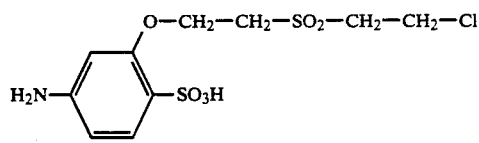
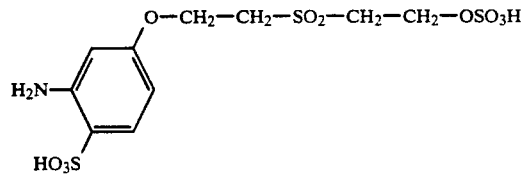
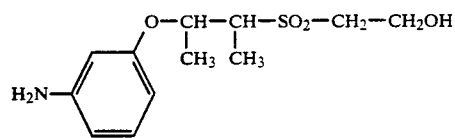
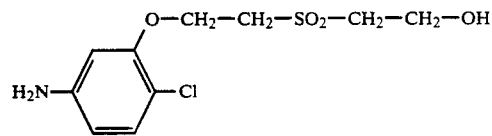
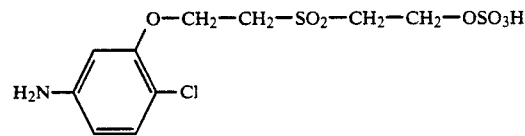
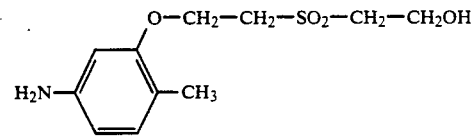
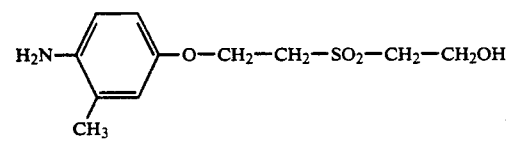
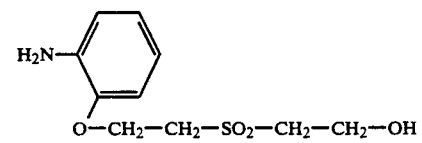
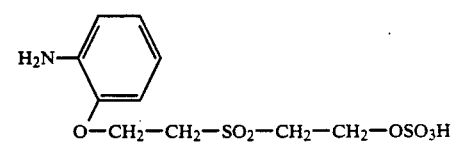

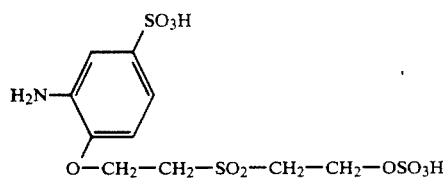
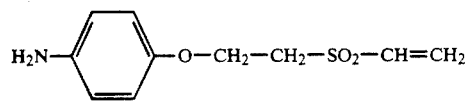
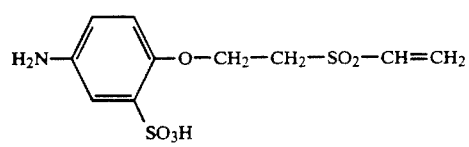
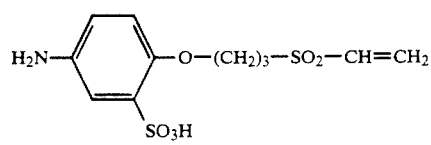
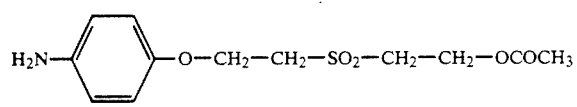
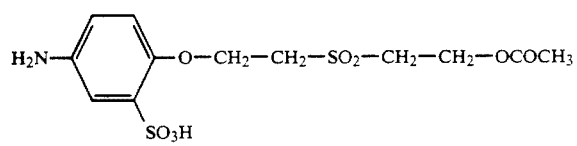
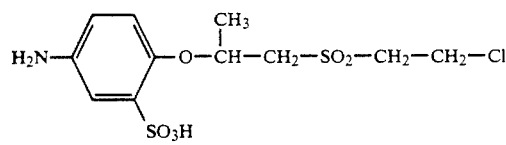
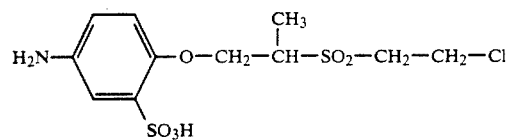
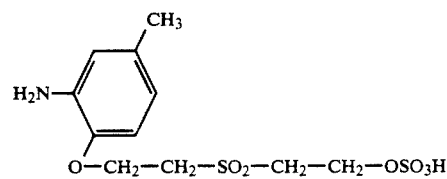
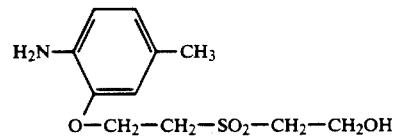
Suitable 1,4-benzoquinones (VI) or (VIII) for condensation with the amines of the formula (IV) or (V) are, for example
2,3,5,6-tetrachloro-1,4-benzoquinone,
2,3,5,6-tetrabromo-1,4-benzoquinone,
2,5-dichloro-3,6-dimethyl-1,4-benzoquinone,
2,5-dichloro-3,6-dimethoxy-1,4-benzoquinone,
2,3,5,6-tetramethoxy-1,4-benzoquinone, 2,3,5,6-tetraphenoxy-1,4-benzoquinone,
2,3,5,6-tetra-(4'-methylphenoxy)-1,4-benzoquinone,
2,3,5,6-tetra-(4'-methoxyphenoxy)-1,4-benzoquinone,
2,5-diacetylamino-3,6-dichloro-1,4-benzoquinone,
2,5-dibenzoylamino-3,6-dichloro-1,4-benzoquinone,
2,3,5,6-tetra-(4'-chlorophenoxy)-1,4-benzoquinone,
2,3,5,6-tetra-4-(3'-methyl-4,-chlorophenoxy)-1,4-benzoquinone,
2-ethyl-3,6-dimethoxy-1,4-benzoquinone,
2-chloro-3,6-dimethoxy-1,4-benzoquinone,
2,3,5-trimethoxy-1,4-benzoquinone,
2,3,5,6-tetra-(4'-nitrophenoxy)-1,4-benzoquinone,
2,5-dimethyl-3,6-dimethoxy-1,4-benzoquinone,,
2-methyl-3,6-dimethoxy-1,4-benzoquinone
2-methyl-5,6-dimethoxy-1,4-benzoquinone,
2-ethyl-3,6-dimethoxy-1,4-benzoquinone,
2-chloro-3-n-propyl-5-methoxy-1,4-benzoquinone,
2-chloro-3,5-dimethoxy-1,4-benzoquinone,
2-methyl-3,5-dichloro-1,4-benzoquinone,
2-methyl-3,5,6-tribromo-1,4-benzoquinone,
2-(4'-methylphenoxy)-3,6-dibromo-1,4-benzoquinone,
2-(3'-methylphenoxy)-3,6-dibromo-1,4-benzoquinone,
2-methyl-3,5,6-trichloro-1,4-benzoquinone,
2-methyl-3-chloro-5-bromo-1,4-benzoquinone,
2-methyl-3,6-dichloro-1,4-benzoquinone,
2-methyl-3,6-dichloro-5-bromo-1,4-benzoquinone,
2-phenyl-3,6-dichloro-1,4-benzoquinone,
2-(4'-methoxyphenyl)-3,6-dichloro-1,4-benzoquinone,
2-(4'-chlorophenyl)-3,6-dichloro-1,4-benzoquinone,
2-(4'-nitrophenyl)-3,6-dichloro-1,4-benzoquinone,
2-(4'-nitrophenyl)-3,5,6-trichloro-1,4-benzoquinone,
2,5-dimethyl-3,6-dibromo-1,4-benzoquinone,
2,5-dimethyl-3-chloro-1,4-benzoquinone,
2-methyl-5-n-propyl-6-bromo-1,4-benzoquinone,
2-methyl-5-isopropyl-3-chloro-1,4-benzoquinone,
2-methyl-5-isopropyl-6-bromo-1,4-benzoquinone and
2-(2,-chlorophenyl)-3,5,6-tribromo-1,4-benzoquinone,
2-methyl-3-methoxy-1,4-benzoquinone,
1,4-benzoquinone,
2-methyl-1,4-benzoquinone,
2-ethyl-1,4-benzoquinone,
2-n-propyl-1,4-benzoquinone,
2-isopropyl-1,4-benzoquinone,
2,2'-ethoxyethyl-1,4-benzoquinone,
2-phenyl-1,4-benzoquinone,
2-(4'-methylphenyl)-1,4-benzoquinone,
2-(4,-methoxyphenyl)-1,4-benzoquinone,
2-(3,-chlorophenyl)-1,4-benzoquinone,
2-(4,-nitrophenyl)-1,4-benzoquinone,
2,5-dimethyl-1,4-benzoquinone,
2-methyl-5-ethyl-1,4-benzoquinone,
2-methyl-3-chloro-1,4-benzoquinone,
2-methyl-6-chloro-1,4-benzoquinone,
2,5-dichloro-3,6-di-(methoxcarbonyl)-1,4-benzoquinone,
2,5-dibromo-3,6-di-(ethoxycarbonyl)-1,4-benzoquinone and 2,3,5,6-tetrafluoro-1,4-benzoquinone.

Reactions of such 1,4-benzoquinones of type (VI) or (VIII) are described in detail in German Offenlegungsschrift (German Published Specification) 2,823,828.

The new dyestuffs are useful products which are distinguished by high tinctorial strength. They are suitable in dispersed or dissolved form for the most diverse intended uses.

As water-soluble compounds, they are of preferred interest for dyeing textile materials containing hydroxyl or amide groups, in particular materials of natural and regenerated cellulose as well as synthetic polyamide and polyurethane fibres, wool and silk.

As water-soluble reactive dyestuffs, the materials mentioned are dyed or printed by the processes generally customary for reactive dyestuffs. Red dyeings and prints which are fast to light and wet processing are then obtained.

The temperature data in the examples are in °C. The formulae of the water-soluble dyestuffs in the description and in the examples are those of the free acids. The dyestuffs are as a rule isolated and used in the form of their alkali metal salts, in particular the lithium, sodium or potassium salts.

The new compounds (IV) and (V) or (XIII) are useful intermediate products for the preparation of dyestuffs. The compounds (IV) and (V) are intermediate products for the preparation of dyestuffs (I). The compounds (XIII) where M'=NHz are suitable, for example, as diazo components for the preparation of azo dyestufts.

EXAMPLE 1

42.8 g of 3-(4-aminophenoxy)-propyl-2-hydroxyethyl sulphone are suspended in 430 ml of water and 65 ml of isopropanol. The mixture is heated to 40°, the pH is brought to 6.0 and 20.3 g of 2,3,5,6-tetrachlorobenzoquinone are added. At a temperature of 40°, the pH in the reaction mixture is kept constantly at 5.8–6.0 with 2N sodium carbonate solution and these conditions are maintained for several hours, until the uptake of sodium carbonate has stopped.

The finely crystalline pale brown precipitate is filtered off with suction, washed with 500 ml of water and 250 ml of methanol and dried at 60° in a circulating air cabinet. The resulting product corresponds to the formula

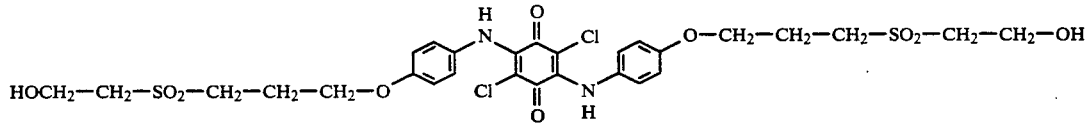

30.0 g of the resulting intermediate product are uniformly introduced into 100 ml of 26% strength oleum at −5 to 0° in the course of 2–3 hours. The temperature is then increased to +20° C. and the mixture is subsequently stirred for some time, until a chromatographic sample indicates no further change and in addition to 2 sulphato groups, 2 sulphonic acid groups have also entered the molecule. The batch is heated to 30° and 23.5 g of potassium peroxodisulphate are introduced in the course of one hour, during which the temperature is kept between 28° and 33°, and stirring is continued for a further 30 minutes at 30° C. until the reaction is complete.

The blue solution formed is introduced into 600 g of ice and 100 ml of water and the brown solution is brought to pH 3 by gradual addition of calcium carbonate and to pH 5.5 by addition of dilute sodium hydroxide solution and freed by filtration from the calcium sulphate which has precipitated. After the gypsum has been washed with water, the combined red filtrates are evaporated to give a dyestuff of the formula minutes until the reaction is complete. The blue solution is stirred into 800 g of ice and the dyestuff is salted out by introduction of 150 g of potassium chloride.

After the mixture has been subsequently stirred for

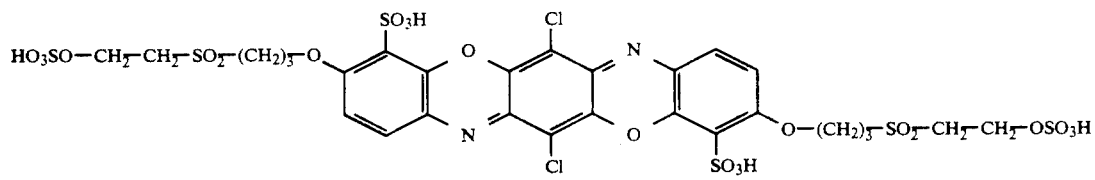

which dyes cellulose fibres in bluish-tinged red shades with good fastness properties.

$\lambda_{max}$ = 538 nm, 505 nm in water.

EXAMPLE 2

50.0 g of β-(4-aminophenoxy)-ethyl-β',-hydroxyethyl sulphone are suspended in 500 ml of water and 75 ml of isopropanol. 25.1 g of 2,3,5,6-tetrachlorobenzoquinone are added to the suspension, the batch is heated to 40° and the pH in the reaction mixture is kept constantly at 6.0-6.2 with 2N sodium carbonate solution. When the condensation has ended, after about 5 hours, the small pale brown needles which have precipitated are filtered off with suction and the filtercake is washed with 1 l of water and 500 ml of methanol and dried at 60° in a circulating air cabinet. The resulting product corresponds to the formula some time, the precipitate is filtered off with suction and the filtercake is covered once or twice with 25% strength potassium chloride solution and then whisked or dissolved in 75 ml of water. 2.7 g of secondary sodium phosphate are added to the solution and the pH is then brought to 5.0-5.5 with dilute sodium hydroxide solution or sodium carbonate solution. The dyestuff can be isolated from the solution by evaporation, or by spray drying after further dilution. It corresponds, in the form of the free acid, to the formula

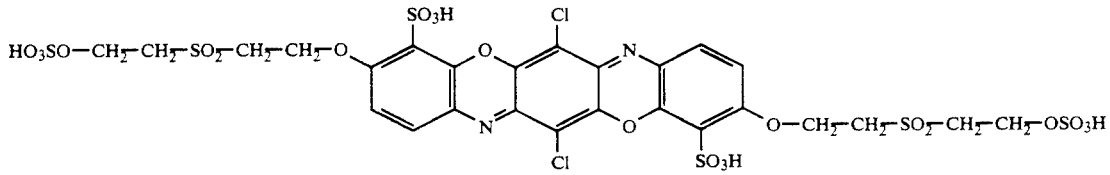

and dyes wool or synthetic polyamide in deep, fast red shades.

$\lambda_{max}$ = 534 nm, 500 nm in water.

The same dyestuff is obtained if the β-(4-aminophenoxy)-ethyl-β'-sulphatoethyl sulphone of Example 6 or the β'-(4-amino-2-sulphophenoxy)-ethyl-β'-sulphatoethyl sulphone of Example 17 is employed instead of the

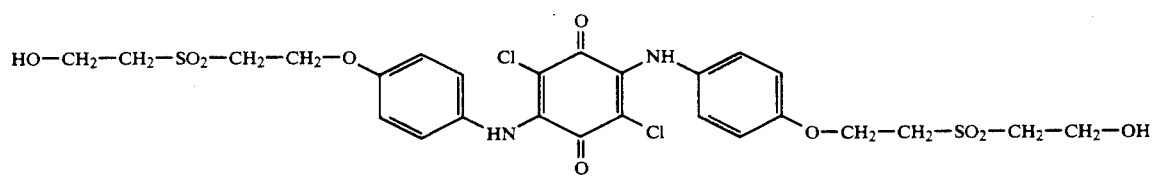

30.0 g of the resulting diarylamino-dichloroquinone are uniformly introduced into 90 ml of 20% strength and 15 ml of 65% strength oleum at −5° to 0° in the course of 2 hours. The temperature is increased to 20° and the mixture is subsequently stirred for some time, until a chromatographic sample indicates no further change and in addition to 2 sulphato groups, 2 sulphonic acid groups have also entered the molecule. The batch is heated to 30°, 24.5 g of potassium peroxodisulphate are introduced in the course of one hour, during which the temperature is kept between 33 and 35°, and after the introduction stirring is continued for a further 15-30

β-(4-aminophenoxy)-ethyl-β'-hyroxyethyl sulphone.

Other dyestuffs of the general formula I are obtained if the aminophenoxyalkyl-β'-hydroxyethyl sulphones listed in the left-hand column of the table or corresponding β'-sulphatoethyl sulfones or amino-sulphophenoxy-alkyl-β-sulphatoethyl sulphones are subjected to condensation reactions with the benzoquinones in the right-hand column, the condensation products are sulphated or sulphonated and sulphated, if appropriate, in sulphuric acid or oleum and the products are then cyclized oxidatively to triphendioxazines, as shown.

TABLE 1

| No. | Sulphone | Benzoquinone |
|---|---|---|
| 1 | H$_2$N—C$_6$H$_4$—O—(CH$_2$)$_4$—SO$_2$—CH$_2$—CH$_2$OH | Chloranil (2,3,5,6-tetrachloro-1,4-benzoquinone) |
| 2 | H$_2$N—C$_6$H$_4$—O—CH(CH$_3$)—CH$_2$—SO$_2$—CH$_2$—CH$_2$OH | ″ |
| 3 | H$_2$N—C$_6$H$_4$—O—CH(CH$_3$)—CH(CH$_3$)—SO$_2$—CH$_2$—CH$_2$—OH | ″ |
| 4 | H$_2$N—C$_6$H$_4$—O—(CH$_2$)$_3$—SO$_2$—CH$_2$—CH$_2$OH | 2,3,5,6-tetrabromo-1,4-benzoquinone |
| 5 | H$_2$N—C$_6$H$_4$—O—CH$_2$—CH(CH$_3$)—SO$_2$—CH$_2$—CH$_2$—CH$_2$OH | 2,3,5,6-tetrachloro-1,4-benzoquinone |
| 6 | H$_2$N—C$_6$H$_4$—O—(CH$_2$)$_6$—SO$_2$—CH$_2$—CH$_2$OH | ″ |
| 7 | H$_2$N—C$_6$H$_4$—O—CH(cyclohexylene)—SO$_2$—CH$_2$—CH$_2$OH | ″ |
| 8 | H$_2$N—C$_6$H$_4$—O—CH$_2$—CH(OH)—CH$_2$—SO$_2$—CH$_2$—CH$_2$OH | ″ |
| 9 | H$_2$N—C$_6$H$_4$—O—CH$_2$—CH$_2$—O—CH$_2$—CH$_2$—SO$_2$—CH$_2$—CH$_2$—OH | 2,3,5,6-tetrachloro-1,4-benzoquinone |
| 10 | H$_2$N—C$_6$H$_4$—O—CH$_2$—CH$_2$—N(CH$_3$)—CH$_2$—CH$_2$—SO$_2$—CH$_2$—CH$_2$OH | ″ |
| 11 | H$_2$N—C$_6$H$_4$—O—CH$_2$—CH$_2$—NH—CH$_2$—CH$_2$—SO$_2$—CH$_2$—CH$_2$OH | ″ |

TABLE 1-continued

| No. | Sulphone | Benzoquinone |
|---|---|---|
| 12 | H₂N—C₆H₄—O—CH₂—CH₂—N(CH₃)—SO₂—CH₂—CH₂OH | ″ |
| 13 | H₂N—C₆H₄—O—CH₂—CH(CH₂OH)—SO₂—CH₂—CH₂—OH | ″ |
| 14 | H₂N—C₆H₄—O—CH₂—CH₂—CH₂—SO₂—CH₂—CH₂OH | 2,3,5,6-tetrakis(phenoxy)-1,4-benzoquinone (H₅C₆O substituents) |
| 15 | 2-amino-5-methyl-phenyl-O—CH₂—CH₂—SO₂—CH₂—CH₂OH | ″ |
| 16 | H₂N—C₆H₄—O—CH₂—CH₂—SO₂—CH₂—CH₂OH | 2,5-dichloro-3,6-bis(acetylamino)-1,4-benzoquinone |
| 17 | ″ | 2,3,5,6-tetramethoxy-1,4-benzoquinone |
| 18 | H₂N—C₆H₄—O—(CH₂)₃—SO₂—CH₂—CH₂OH | 2,5-dichloro-3,6-dimethyl-1,4-benzoquinone |
| 19 | ″ | 2,3,5,6-tetramethoxy-1,4-benzoquinone |
| 20 | ″ | 2,5-dichloro-3,6-bis(phenoxy)-1,4-benzoquinone (Cl and OC₆H₅ substituents) |

TABLE 1-continued

| No. | Sulphone | Benzoquinone |
|---|---|---|
| 21 | H$_2$N—C$_6$H$_4$—O—CH(CH$_3$)—CH(CH$_3$)—SO$_2$—CH$_2$—CH$_2$OH | 2,3,5,6-tetrakis(phenoxy/phenyl)-1,4-benzoquinone (H$_5$C$_6$O, OC$_6$H$_5$, H$_6$C$_6$O, OC$_6$H$_5$) |
| 22 | H$_2$N—C$_6$H$_4$—O—CH$_2$—CH$_2$—SO$_2$—CH$_2$—CH$_2$OH | 1,4-benzoquinone |
| 23 | H$_2$N—C$_6$H$_3$(SO$_3$H)—O—(CH$_2$)$_3$—SO$_2$—CH$_2$—CH$_2$—OSO$_3$H | tetrachloro-1,4-benzoquinone |
| 24 | H$_2$N—C$_6$H$_3$(SO$_3$H)—O—CH$_2$—CH$_2$—SO$_2$—CH$_2$—CH$_2$—OSO$_3$H | tetrachloro-1,4-benzoquinone |
| 25 | H$_2$N—C$_6$H$_3$(SO$_3$H)—O—CH$_2$—CH$_2$—SO$_2$—CH$_2$—CH$_2$OH | " |
| 26 | H$_2$N—C$_6$H$_3$(SO$_3$H)—O—(CH$_2$)$_3$—SO$_2$—CH$_2$—CH$_2$OH | " |
| 27 | H$_2$N—C$_6$H$_3$(SO$_3$H)—O—(CH$_2$)$_6$—SO$_2$—CH$_2$—CH$_2$OH | " |
| 28 | H$_2$N—C$_6$H$_3$(CH$_3$)—O—CH$_2$—CH$_2$—SO$_2$—CH$_2$—CH$_2$—OH | " |
| 29 | H$_2$N—C$_6$H$_3$(CH$_3$)—O—CH$_2$—CH$_2$—SO$_2$—CH$_2$—CH$_2$OH | tetrachloro-1,4-benzoquinone |

TABLE 1-continued

| No. | Sulphone | Benzoquinone |
|---|---|---|
| 30 | 5-amino-2-chlorophenyl-O-CH$_2$-CH$_2$-SO$_2$-CH$_2$-CH$_2$OH | " |
| 31 | 4-amino-3-chlorophenyl-O-CH$_2$-CH$_2$-CH$_2$-SO$_2$-CH$_2$-CH$_2$OH | " |
| 32 | 5-amino-2-(...)-benzoic acid: H$_2$N–C$_6$H$_3$(COOH)–O-CH$_2$-CH$_2$-CH$_2$-SO$_2$-CH$_2$-CH$_2$OH | " |
| 33 | 4-amino-2-methylphenyl-O-CH$_2$-CH$_2$-SO$_2$-CH$_2$-CH$_2$-OH | tetrachloro-1,4-benzoquinone |
| 34 | 4-amino-2-chlorophenyl-O-CH$_2$-CH$_2$-SO$_2$-CH$_2$-CH$_2$OH | " |
| 35 | 4-amino-3-methylphenyl-O-CH$_2$-CH$_2$-SO$_2$-CH$_2$-CH$_2$OH | " |
| 36 | 3-aminophenyl-O-CH$_2$-CH$_2$-SO$_2$-CH$_2$-CH$_2$OH | " |
| 37 | 5-amino-2-methylphenyl-O-CH$_2$-CH$_2$-SO$_2$-CH$_2$-CH$_2$OH | tetrachloro-1,4-benzoquinone |
| 38 | 2-aminophenyl-O-CH$_2$-CH$_2$-SO$_2$-CH$_2$-CH$_2$OH | " |
| 39 | 4-aminophenyl-O-(CH$_2$)$_5$-SO$_2$-CH$_2$-CH$_2$OH | " |
| 40 | 4-aminophenyl-O-C(CH$_3$)$_2$-CH$_2$-SO$_2$-CH$_2$-CH$_2$OH | " |

TABLE 1-continued

| No. | Sulphone | Benzoquinone |
|---|---|---|
| 41 | 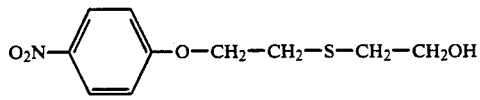 O—(CH₂)₄—SO₂—CH₂—CH₂OH with H₂N-phenyl | tetrachloro-benzoquinone (Cl, Cl, Cl, Cl) |
| 42 | O—(CH₂)₃—SO₂—CH₂—CH₂OH with NH₂-phenyl | " |

EXAMPLE 3

The β-(4-aminophenoxy)-ethyl-β'-hydroxyethyl sulphone used at the start of Example 2 can be prepared in the following manner:

100 g of 1-(2-hydroxyethoxy)-4-nitrobenzene (prepared by reaction of 4-nitrophenol with ethylene oxide) are introduced into 300 ml of thionyl chloride. 1 ml of dimethylformamide is added and the mixture is heated under reflux for 1½ hours. After cooling, the resulting solution is stirred into 2 kg of ice-water so that the temperature does not exceed 0°–5°. The white precipitate is filtered off with suction, washed neutral with water and dried in vacuo.

42 g of the 1-(2-chloroethoxy)-4-nitrobenzene prepared are heated under reflux in 100 ml of acetonitrile with 17.8 g of 2-mercaptoethanol and 33 g of potassium carbonate for 6 hours, until the replacement of the chlorine atom by the mercaptoethanol radical is complete.

If the batch is poured into ten times the amount of water, a yellow oil separates out in a virtually quantitative yield and can be washed out thoroughly with water. The product corresponds to the formula O₂N—⟨phenyl⟩—O—CH₂—CH₂—S—CH₂—CH₂OH $^1$H-NMR in D₆-DMSO (TMS as the internal standard)

| | |
|---|---|
| δ = 2.68 ppm | (2H, t) |
| δ = 2.94 ppm | (2H, t) |
| δ = 3.54–3.61 ppm | (2H, q) |
| δ = 4.27 ppm | (2H, t) |
| δ = 4.82 ppm | (2H, m) |
| δ = 7.13 ppm | (2H, m) |
| δ = 8.16 ppm | (2H, m) |

For further oxidation, it is not necessary to isolate the sulphide.

After the above replacement reaction, the batch can be diluted with 250 ml of water. This gives a yellowish two-phase mixture, to which a neutralized solution of 0.5 g of tungstic acid in 10 ml of water and 5.0 g of sodium acetate are added. A pH of 6.0 is established in the mixture by addition of acetic acid and 40.5 g of 35% strength hydrogen peroxide are then added dropwise at 45° in the course of one hour. Thereafter, the mixture is heated at 60° for 3 hours, a further 4.0 g of 35% strength hydrogen peroxide are then subsequently added if necessary and the temperature is kept at 60° until the oxidation has ended.

The acetonitrile is distilled off from the resulting two-phase mixture under reduced pressure, after which the sulphone of the formula

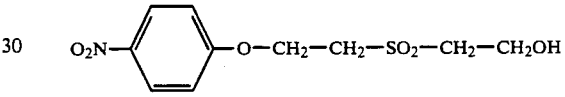

crystallizes out.

Melting point: 93°–94° from methylene chloride/n-hexane 10:2

$^1$H-NMR in D₆-DMSO (TMS as the internal standard).

| | |
|---|---|
| δ = 3.36 ppm | (2H, t) |
| δ = 3.63 ppm | (2H, t) |
| δ = 3.84–3.91 ppm | (2H, q) |
| δ = 4.53 ppm | (2H, t) |
| δ = 5.21 ppm | (1H, t) |
| δ = 7.19 ppm | (2H, m) |
| δ = 8.21 ppm | (2H, m) |

80 g of the above β-(4-nitrophenoxy)-ethyl-β'-hydroxyethyl sulphone are placed under a hydrogen pressure of 50–70 bar in 240 ml of methanol in an autoclave after addition of 4 g of Raney nickel. The autoclave is heated up to 60° in the course of 1–2 hours and the hydrogen pressure is maintained until the reaction has ended. 200 ml of methanol are added to the contents of the autoclave and the suspension is clarified by removing the nickel at the boiling point. The amine of the formula

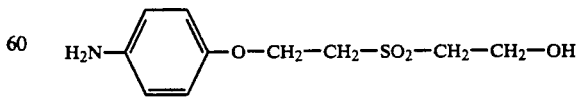

crystallizes out of the filtrate on cooling and is filtered off with suction from the cooled mixture, and can be washed with a little cold methanol.

Melting point: 114–115°.

$^1$H-NMR in D₆-DMSO (TMS as the internal standard).

| | |
|---|---|
| δ = 3.30 ppm | (2H, t) |
| δ = 3.54 ppm | (2H, t) |
| δ = 3.78–3.85 ppm | (2H, q) |
| δ = 4.18 ppm | (2H, t) |
| δ = 4.65 ppm | (2H, s) |
| δ = 5.14 ppm | (1H, t) |
| δ = 6.49 ppm | (2H, m) |
| δ = 6.66 ppm | (2H, m) |

Instead of the 1-(2-chloroethoxy)-4-nitrobenzene employed above, it is also possible to react 1-(2-bromoethoxy)-4-nitrobenzene and β-(4-nitrophenoxy)-ethyl p-toluene-sulphonate analogously with 2-mercaptoethanol to give β-(4-nitrophenoxy)-ethyl-β'-hydroxyethyl sulphide.

If instead of the abovementioned 2-(4-nitrophenoxy)-ethyl halides or sulphonates, corresponding 2-(4-acetaminophenoxy)-ethyl halides or sulphonates are reacted with 2-mercaptoethanol, the intermediates are then oxidized with hydrogen peroxide in water or glacial acetic acid and the acetylamino group is hydrolyzed in hot dilute hydrochloric acid, p-(4-aminophenoxy)-ethyl-β'-hydroxyethyl sulphone is likewise obtained.

EXAMPLE 4

42.0 g of the 1-(2-chloroethoxy)-4-nitrobenzene prepared according to Example 3 are boiled under reflux for several hours with 21.3 g of 2-mercaptoethanol and 14.1 g of powdered potassium hydroxide in 160 ml of ethanol under a nitrogen atmosphere until a chromatographic sample indicates complete replacement of the chlorine atom in the educt by the β-hydroxyethylmercaptide radical.

The resulting suspension is diluted with 320 ml of water, a neutralized solution of 0.5 g of tungstic acid in 10 ml of water is added to the resulting emulsion and, after addition of 2.5 g of sodium acetate, the pH of the mixture is brought to 5.5 with acetic acid. To oxidize the sulphide, 55 ml of 35% strength hydrogen peroxide are added dropwise at 50°–60° in the course of one hour and the temperature is then kept at 60° for a further 3–4 hours, until oxidation of the sulphoxide formed as the intermediate product to the sulphone is complete.

The ethanol is distilled off from the clear solution. When seeded at room temperature, the emulsion obtained deposits the sulphone of the formula

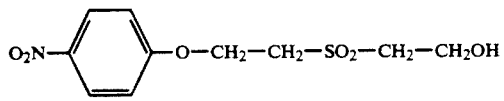

in crystals, which are dried, if appropriate, after filtration with suction and washing with water.

Catalytic reduction with hydrogen and Raney nickel in accordance with the instructions in Example 3 leads to the corresponding amino compound.

EXAMPLE 5

30.0 g of 1-(2-hydroxyethoxy)-4-nitrobenzene are dissolved in 60 ml of pyridine. 18.9 g of methanesulphonyl chloride are added dropwise at 10°–15° in the course of 15 minutes and the temperature is then increased to 20°. The reaction has ended after 3 hours. 60 ml of water are added dropwise to the solution formed, after which the methanesulphonate crystallizes in attractive needles. The crystals are filtered off with suction and washed with water to give a product of the formula

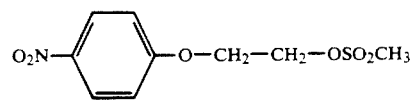

of melting point: 70°–71.5°.

11.7 g of 2-mercaptoethanol are dissolved in 150 ml of 1N sodium hydroxide solution. 30.0 g of powdered methanesulphonate of the above formula are added to the solution and the resulting suspension is placed under a nitrogen atmosphere. It is heated at 70° for several hours, until the replacement of the methanesulphonate is complete. A yellow oil of the formula

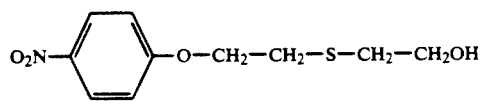

which is identical to the sulphide of Example 3, has formed. The product is separated off, washed with dilute sodium carbonate solution and water and then oxidized in an aqueous emulsion with 23 g of 35% strength hydrogen peroxide in the manner described in Example 3 with addition of catalytic amounts of tungstic acid to give the sulphone described in that example.

EXAMPLE 6

35.0 g of 2-(4-aminophenoxyethyl)-2-hydroxyethyl sulphone of Example 3 are introduced into 70 ml of 96% strength sulphuric acid at 0°–5°. The mixture is stirred for 2 hours and the resulting solution is introduced into 420 g of ice. The crystalline precipitate is filtered off with suction, washed with 25% strength sodium chloride solution until free from sulphate and dried at 50° in vacuo. The resulting product corresponds to the formula

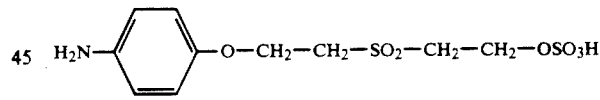

or its inner salt.

$^1$H-NMR in $D_6$-DMSO (TMS as the internal standard).

| | |
|---|---|
| δ = 3.51 ppm | (2H, t) |
| δ = 3.62 ppm | (2H, t) |
| δ = 4.12 ppm | (2H, t) |
| δ = 4.35 ppm | (2H, t) |
| δ = 7.04–7.08 ppm | (2H, d) |
| δ = 7.27–7.31 ppm | (2H, d) |
| δ = 10.1 ppm | (3H, s) |

EXAMPLE 7

The 3-(4-aminophenoxy)-propyl-2-hydroxyethyl sulphone used at the start of Example 1 can be obtained in the following manner:

111 g of 1-(3 hydroxypropoxy)-4-nitrobenzene (prepared, for example, from 4-nitrofluorobenzene and 1,3-propanediol or from 4-nitrophenol and 3-bromo- or 3-chloro-1-propanol) are dissolved in 113 ml of pyridine. A solution of 102 g of p-toluenesulphonyl chloride in 107 ml of pyridine are added dropwise to the solution in the course of 30 minutes, starting at 5°, and the temperature is allowed to rise to 20° by the heat of reaction and crystallization. The crystal sludge is cooled to 0° and filtered off with suction and the crystals are washed with 400 ml of ice-cold methanol and then with water and dried at 50° in vacuo.

Melting point: 136°–139°.

85 g of the resulting toluenesulphonate are heated under reflux at 84° in 240 ml of acetonitrile with 21.2 g of 2-mercaptoethanol and 38.5 g of potassium carbonate for 2.5 hours. After the mixture has been poured into 1 l of water, a yellow oil separates out, which corresponds to the formula

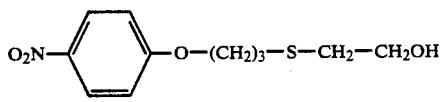

and can be taken up in methylene chloride. After the organic phase has been dried over sodium sulphate and the methylene chloride has been distilled off, the sulphide can be obtained as an oil which solidifies at 43°–46°.

$^1$H-NMR in D$_6$-DMSO (TMS as the internal standard).

| | |
|---|---|
| δ = 1.97–2.08 ppm | (2H, m) |
| δ = 2.58–2.73 ppm | (4H, m) |
| δ = 3.55 ppm | (2H, m) |
| δ = 4.20 ppm | (2H, t) |
| δ = 4.,81 ppm | (1H, s) |
| δ = 7.11–7.15 ppm | (2H, d) |
| δ = 8.16–7.20 ppm | (2H, d) |

Instead of the tosyl ester, it is also possible to react 3-(4-nitrophenoxy)-1-propyl chloride or -1-propyl bromide, which are prepared from 4-nitrophenol and the 1,3-dihalogenopropanes, with 2-mercaptoethanol analogously to Example 3 to give the above sulphide.

To oxidize the sulphide, a procedure is in general followed in which the oil-water mixture obtained after the mercaptide replacement reaction is oxidized with 50.0 g of 35% strength hydrogen peroxide directly under tungstic acid catalysis at 60° analogously to Example 3. After cooling, the sulphone obtained as crystals, of the formula

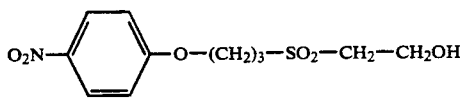

is isolated.

Melting point: 104°–106°.

$^1$H-NMR in D$_6$-DMSO (TMS as the internal standard).

| | |
|---|---|
| δ = 2.15–2.27 ppm | (2H, m) |
| δ = 3.26–3.38 ppm | (4H, m) |
| δ = 3.78–3.85 ppm | (2H, q) |
| δ = 4.23 ppm | (2H, t) |
| δ = 5.15 ppm | (1H, t) |
| δ = 7.09–7.13 ppm | (2H, d) |
| δ = 8.15–8.19 ppm | (2H, d) |

Another variant for preparation of the above sulphone comprises a procedure in which 61 g of the 8-(4-nitrophenoxy)-propyl-β-hydroxyethyl sulphide which is obtained above and has been freed from water are dissolved in 122 ml of glacial acetic acid and oxidized with 47 g of 35% strength H$_2$O$_2$, starting at 30°, the mixture subsequently being heated at 40° for several hours to complete the oxidation, until the sulphoxide formed as the intermediate product is no longer detectable by chromatography. The sulphone is isolated by dilution of the batch with 125 ml of water, filtration with suction and washing with water, whereupon a product of melting point: 104°–106° which is identical to the sulphone described above is obtained.

50 g of the above nitrosulphone are reduced in 200 ml of methanol, after addition of 2.5 g of Raney nickel, in an autoclave at 60° under a hydrogen pressure of 60 bar. When no further hydrogen is taken up, the contents of the autoclave are diluted with 200 ml of methanol and 100 ml of water and the nickel is filtered off with suction at the boiling point. The amino compound of the formula

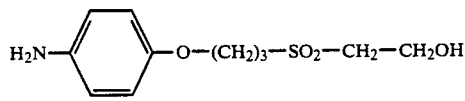

crystallizes out of the filtrate in attractive needles of melting point: 136.5°–138°.

$^1$H-NMR in D$_6$-DMSO (TMS as the internal standard).

| | |
|---|---|
| δ = 2.02–2.14 ppm | (2H, m) |
| δ = 3.23–3.29 ppm | (4H, m) |
| δ = 3.77–3.84 ppm | (2H, q) |
| δ = 3.91 ppm | (2H, t) |
| δ = 4.60 ppm | (2H, s) |
| δ = 5.14 ppm | (1H, t) |
| δ = 6.47–6.51 ppm | (2H, d) |
| δ = 6.62–6.66 ppm | (2H, d) |

EXAMPLE 8

50 g of β-(4-nitrophenoxy)-β'-hydroxyethyl sulphide are stirred into 300 ml of 20% strength hydrochloric acid. A slow stream of chlorine is passed into the emulsion formed and the heat of reaction formed is removed by external cooling so that the temperature is kept at 30°. Attractive crystals soon separate out of the emulsion. When no further chlorine is consumed, the completeness of the oxidation is checked by chromatography. The resulting product is filtered off with suction and washed free from chloride with water. It corresponds to the formula

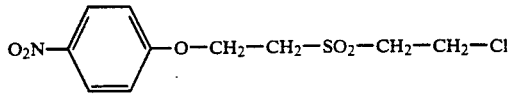

Melting point: 85°–86°.

$^1$H-NMR in D$_6$DMSO (TMS as the internal standard).

| | |
|---|---|
| δ = 3.73–3.82 ppm | (4H, m) |
| δ = 3.99 ppm | (2H, t) |
| δ = 3.53 ppm | (2H, t) |
| δ = 7.17–7.21 ppm | (2H, d) |
| δ = 8.19–8.23 ppm | (2H, d) |

EXAMPLE 9

75.0 g of 4-nitrophenol are dissolved in 750 ml of water and 130 ml of 4N sodium hydroxide solution at pH 8.5 and 80°. 62.5 g of propylene oxide are added dropwise to the solution in the course of 8 hours, during which the pH is kept at 8.5 by dropwise addition of 2N sulphuric acid. If a little nitrophenol is still present after maintaining pH 8.5 and 80° overnight, a further 16 g of propylene oxide are subsequently added, if appropriate, and the reaction conditions are maintained until the educt is no longer detectable. An oil has separated out of the aqueous phase as the product and is separated off and dried. The resulting product is an isomer mixture of the following substances.

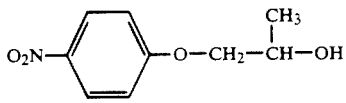

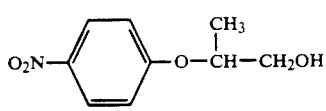

72.0 g of the resulting oil are dissolved in 73 ml of pyridine. A solution of 69.7 g of p-toluenesulphonyl chloride in 73 ml of pyridine is added dropwise at 10°-15°, while cooling, and the mixture is then stirred overnight at 0°-5°. Crystals precipitate out of the initially clear solution and are filtered off with suction in the cold and washed with 200 ml of ice-cold methanol and then with water. 56.5 g of the pure isomer of the formula

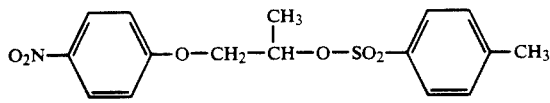

of melting point: 84°-86° are obtained.

$^1$H-NMR in D$_6$-DMSO (TMSO as the internal standard).

| | |
|---|---|
| δ = 1.41 ppm | (3H, d) |
| δ = 2.43 ppm | (3H, s) |
| δ = 4.01–4.11 ppm | (2H, m) |
| δ = 4.82–4.93 ppm | (1H, m) |
| δ = 6.73–6.76 ppm | (2H, d) |
| δ = 7.29–7.33 ppm | (2H, d) |
| δ = 7.73–7.76 ppm | (2H, d) |
| δ = 8.07–8.11 ppm | (2H, d) |

If the combined mother liquor and methanol washings are diluted with 1 l of water after the above toluenesulphonate has been separated off, and the emulsion is extracted with methylene chloride, the extract is dried, the solvent is evaporated off, 100 ml of methanol are added to the residue and the crystals which have precipitated are isolated, a further 50.8 g of an isomer mixture of the formulae

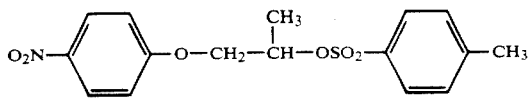

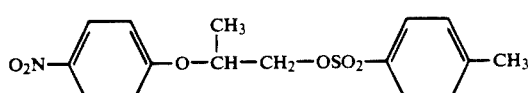

which melts between 68° and 72° can be obtained.

56.0 g of the above isomer-free toluenesulphonate of melting point: 84°-86° are heated under reflux in 150 ml of acetonitrile with 13.0 g of 2-mercaptoethanol and 23 g of potassium carbonate under a nitrogen atmosphere for several hours until replacement of the tosylate by the β-hydroxyethylmercaptide radical is complete. After the batch has been poured into 750 ml of water, a yellow oil of the following formula separates out:

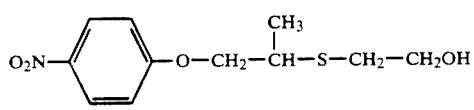

A neutralized solution of 0.3 g of tungstic acid in 10 ml of water and 3 g of sodium acetate is added to the resulting oil-water mixture, the pH in the mixture is brought to 6.0 with acetic acid us the mixture is oxidized with 31.6 g of 35% strength hydrogen peroxide at 45°, at the beginning, to 60°. The sulphone of the formula

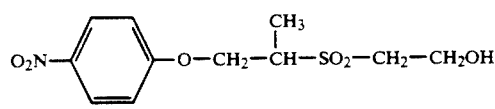

is also obtained as an oil, which is separated off, dissolved in 150 ml of methanol and reduced with 3 g of Raney nickel under a hydrogen pressure of 60 bar at 50°. After chromatographic testing for completeness of the reduction, the methanol is removed by vacuum distillation in a rotary evaporator.

The amine of the formula

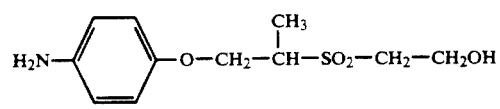

again as an oil, remains.

If the same reaction sequence is carried out directly with the toluenesulphonate isomer mixture obtained instead of with the isomer-free toluenesulphonate which has been separated off, mercaptide replacement, oxidation of the sulphide mixture, and reduction of the nitrosulphone isomers again gives an isomer mixture as an oil, in which the components

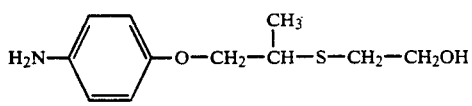

or

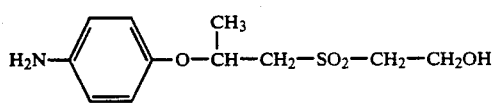

are present in a ratio of about 4:1.

EXAMPLE 11

60.0 g of 4-nitrophenol are dissolved in 600 ml of water and 107 ml of 2N sodium hydroxide solution at 80° and pH 8.5.

94 g of trans-2,3-butylene oxide are added dropwise at 80° in the course of 24 hours and at the same time the pH is kept at 8.5 with 2N sulphuric acid. When the reaction has ended, an oil has separated out of the aqueous phase and is isolated and dried.

$^1$H-NMR in D$_6$-DMSO (TMS as the internal standard).

| | |
|---|---|
| δ = 1.12–1.15 ppm | (3H, d) |
| δ = 1.23–1.25 ppm | (3H, d) |
| δ = 3.72–3.83 ppm | (1H, m) |
| δ = 4.40–4.49 ppm | (1H, m) |
| δ = 4.88–4.90 ppm | (1H, d) |
| δ = 7.09–7.13 ppm | (2H, d) |
| δ = 8.12–8.16 ppm | (2H, d) |

75.0 g of the resulting oil are dissolved in 75 ml of pyridine. A solution of 67.7 g of p-toluenesulphonyl chloride in 67 ml of pyridine is added dropwise and the temperature is kept at 10°. After the mixture has been stirred at 0°–5° for several hours, the crystals which have precipitated are filtered off with suction at 0°, washed with 200 ml of ice-cold methanol and then with water and dried at 50° in vacuo.

Melting point: 116°–118 °.

$^1$H-NMR in D$_6$-DMSO (TMS as the internal standard).

| | |
|---|---|
| δ = 1.27–1.30 ppm | (3H, d) |
| δ = 1.36–1.38 ppm | (3H, d) |
| δ = 2.42 ppm | (3H, s) |
| δ = 4.48–4.57 ppm | (1H, m) |
| δ = 4.67–4.77 ppm | (1H, m) |
| δ = 6.74–6.78 ppm | (2H, d) |
| δ = 7.27–7.31 ppm | (2H, d) |
| δ = 7.70–7.74 ppm | (2H, d) |
| δ = 8.07–8.11 ppm | (2H, d) |

100 g of the resulting toluenesulphonate are heated under reflux for 24 hours in 300 ml of acetonitrile with 24 g of 2-mercaptoethanol and 43.5 g of potassium carbonate under a nitrogen atmosphere until the educt has disappeared and the replacement by the β-hydroxyethylmercaptide radical is complete. The batch is one poured into 75 ml of water, after which the sulphide of the formula

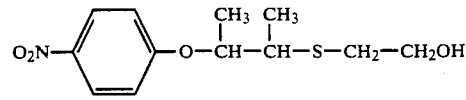

separates out as an oil.

A neutralized solution of 1.0 g of tungstic acid in 20 ml of water is added to the oil-water mixture and, after addition of 3 g of sodium acetate, the pH is brought to 6.0 with acetic acid.

Oxidation with 58 g of 30% strength hydrogen peroxide at 45°–60° analogously to the instructions in Example 3 gives the sulphone of the formula

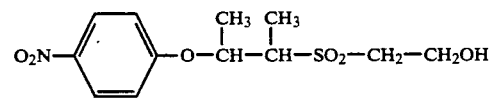

which is obtained as an oil and is separated off, washed with water and dissolved in 400 ml of methanol for catalytic reduction. After addition of 5 g of Raney nickel, the nitro compound is reduced at 50° under a hydrogen pressure of 60 bar. After the nickel has been filtered off, the methanol is distilled off from the filtrate in vacuo. The compound of the formula

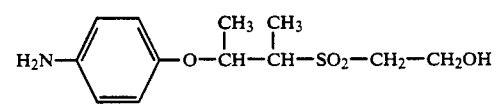

remains as an oily residue.

EXAMPLE 12

The compound of Example 3 or 4, of the formula

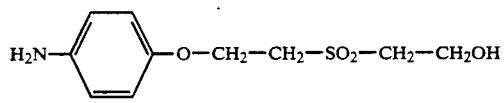

can also be obtained by a procedure in which 45.0 g of 4-nitrofluorobenzene are added dropwise to a mixture of 200 ml of acetonitrile, 115 g of bis-(2-hydroxyethyl) sulphide and 18.0 g of powdered potassium hydroxide at 25° and the reaction mixture is stirred at 25° for 4 hours. When the reaction has ended, the mixture is poured into 2 l of water and the crude β-hydroxyethyl-β'-(4-nitrophenoxy)-ethyl sulphide which has precipitated is separated off as a yellow oil and washed with water.

It is dissolved in 150 ml of glacial acetic acid and oxidized to the sulphone with 85 g of 35% strength hydrogen peroxide at 40°–45°. Thereafter, bis-2-(4-nitrophenoxy)-ethyl sulphone formed as a by-product from the symmetric sulphide has precipitated in the form of needles. The bis-product is separated off by filtration and the nitrosulphone of the formula

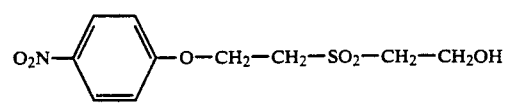

EXAMPLE 13

154 g of 1-(2-hydroxyethoxy)-3-nitrobenzene (prepared by of 3-nitrophenol with 2-chloroethanol at 70-80° and pH 8.5 in water) are introduced into 460 ml of thionyl chloride. When the evolution of gas has ended, 4 ml of dimethylformamide are added and the mixture is heated under reflux for 2 hours. The majority of the thionyl chloride is now distilled off from the reaction mixture and the residue which remains is introduced into 2 kg of ice. The reaction product which has separated out in solid form is comminuted, washed thoroughly neutral with water and dried at 40° in vacuo.

Melting point: of the crude product 57°–58°.

126 g of the 1-(2-chloroethoxy)-3-nitrobenzene prepared in this way are heated to 70° in 630 ml of acetonitrile with 48 ml of 2-mercaptoethanol and 9.9 g of potassium carbonate under a nitrogen atmosphere. After 5 hours, 12 ml of 2-mercaptoethanol and 25 g of potassium carbonate are subsequently added and the reaction is brought to completion at 70° under chromatographic control. When the reaction has ended, the batch is diluted with 2.2 l of water. The honey-yellow oil which has precipitated is separated off and washed with water and, after being dissolved in methylene chloride, can be dried over sodium sulphate, or can be freed from the water in vacuo.

The reaction of the 2-chloroethoxy compound with 2mercaptoethanol can also be carried out in the same volume of ethanol as the solvent instead of in acetonitrile.

The compound

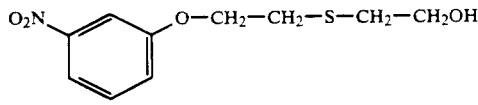

is likewise obtained as an oil.

$^1$H-NMR in D$_6$-DMSO (TMS as the internal standard).

| | |
|---|---|
| δ = 2.71 ppm | (2H, t) |
| δ = 2.96 ppm | (2H, t) |
| δ = 3.57–3.65 ppm | (2H, q) |
| δ = 4.27 ppm | (2H, t) |
| δ = 4.84 ppm | (1M, t) |
| δ = 7.38–7.43 ppm | (1H, m) |
| δ = 7.56 ppm | (1H, t) |
| δ = 7.69 ppm | (1H, t) |
| δ = 7.78–7.83 ppm | (1H, m) |

140.6 g of the oil obtained above are emulsified in 600 ml of water. After addition of 7.2 g of sodium acetate, the pH is brought to 5.2 with about 1.4 ml of glacial acetic acid.

A catalyst solution which has been prepared by dissolving 1.2 g of tungstic acid in 24 ml of water and 1.2 ml of 50% strength sodium hydroxide solution and bringing the pH to 5.2 by means of glacial acetic acid is added.

104 ml of 35% strength hydrogen peroxide are added dropwise to this emulsion at 55°–60° in the course of one hour. The temperature is then still kept at 60°, after 4 hours a further 20 ml of 35% strength hydrogen peroxide are subsequently added and the temperature is maintained for a further 2 hours until a chromatographic sample indicates no further sulphoxide intermediate product. The mixture is cooled to 5° and the emulsion formed deposits crystals which are isolated, comminuted and washed with ice-cold water. A product of the formula

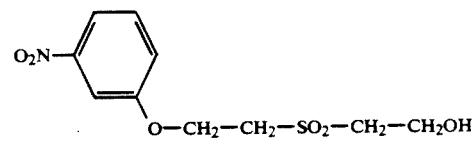

is obtained

Melting point: 89°–91° (after recrystallization from 5 volumes of methanol and 2 volumes of water).

$^1$H-NMR in D$_6$-DMSO (TMS as the internal standard).

| | |
|---|---|
| δ = 3.38 ppm | (2H, t) |
| δ = 3.72 ppm | (2H, t) |
| δ = 3.83–3.90 ppm | (2H, q) |
| δ = 4.52 ppm | (2H, t) |
| δ = 5.19 ppm | (1H, t) |
| δ = 7.43–7.49 ppm | (1H, m) |
| δ = 7.60 ppm | (1H, t) |
| δ = 7.78 ppm | (1H, m) |
| δ = 7.82–7.86 ppm | (1H, m) |

142 g of the resulting nitro compound are placed under a hydrogen pressure of 70 bar in 600 ml of methanol after addition of 10 g of Raney nickel and the temperature is increased to 60°. The hydrogen pressure is kept constant until the consumption of hydrogen has ended and, after cooling, the mixture is let down, the resulting suspension is clarified by removal of the Raney nickel and the filtrate is evaporated in a rotary evaporator until distribution of the solvent is complete.

The product of the formula

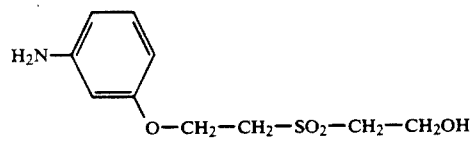

is obtained as a viscous oil which crystalline only after standing for several days. Melting point: 70°–72° (from 4 volumes of isopropanol)

$^1$H-NMR in D$_6$-DMSO (TMS as the internal standard).

| | |
|---|---|
| δ = 3.30 ppm | (2H, t) |
| δ = 3.57 ppm | (2H, t) |
| δ = 3.78–3.85 ppm | (2H, q) |
| δ = 4.21 ppm | (2H, t) |
| δ = 5.04 ppm | (2H, s) |
| δ = 5.14 ppm | (1H, t) |
| δ = 6.06–6.16 ppm | (3 × 1H, m) |
| δ = 6.84–6.91 ppm | (1H, t) |

EXAMPLE 14

50 g of the oil, obtained in Example 13, of the compound

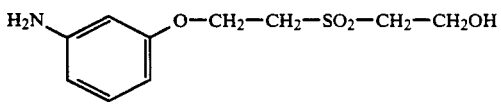

are allowed to run in portions into 125 ml of 96% strength sulphuric acid at 0°. The mixture is subsequently stirred at this temperature for 2 hours and the resulting solution is then poured onto 900 g of ice. Roundish crystals separate out. After subsequently stirring for a short time, the crystals are filtered off ice-cold with suction and the resulting product is washed with isopropanol or 25% strength sodium chloride solution until free from sulphuric acid. It corresponds to the formula

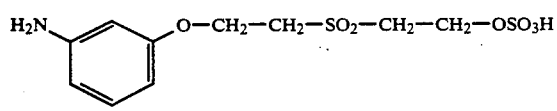

It is dried in vacuo.

$^1$H-NMR in D$_6$-DMSO (TMS as the internal standard).

| | |
|---|---|
| $\delta$ = 3.40 ppm | (2H, t) |
| $\delta$ = 3.63 ppm | (2H, t) |
| $\delta$ = 4.12 ppm | (2H, t) |
| $\delta$ = 4.36 ppm | (2H, t) |
| $\delta$ = 6.89–6.92 ppm | (2 × 1H, m?) |
| $\delta$ = 6.99–7.02 ppm | (1H, m) |
| $\delta$ = 7.35–7.41 ppm | (1H, t) |

EXAMPLE 15

About 80 ml of 50% strength sodium hydroxide solution are added to 250 g of 2-nitrophenol in 2,500 ml of water until the pH is 8.5.

420 ml of 2-chloroethanol are allowed to run in portions into the resulting solution at 80° in the course of 8 hours, during which the pH is kept at 8.5 with sodium hydroxide solution, and the mixture is heated at 80° under these conditions for a further 4 hours until the educt has practically disappeared. The resulting oil of 1-(2-hydroxyethoxy)-2-nitrobenzene is allowed to settle at room temperature and is washed several times with water, traces of water being removed by heating in vacuo up to 70°.

800 ml of thionyl chloride are added to 280 g of the resulting oil at 20°-25° in the course of 30 minutes, with gentle cooling. After addition of 5 ml of dimethylformamide, the mixture is heated at about 80° under reflux for 3 hours. After cooling, the resulting solution is stirred into 5 kg of ice and the oil initially obtained soon solidifies to crystal crumbs. The solid mass is filtered off with suction, comminuted, washed neutral with water and dried in vacuo.

252 g of the resulting 1-(2-chloroethoxy)-2-nitrobenzene are heated at 70° in 1,000 ml of acetonitrile with 26 ml of 2-mercaptoethanol and 198 g of potassium carbonate under a nitrogen atmosphere for 4 hours. 24 ml of 2-mercaptoethanol and 50 g of potassium carbonate are then subsequently added and the mixture is heated under reflux at 80° for a further 4 hours. After cooling, the batch is diluted with 4 l of water and the oil which has separated out is separated off, washed with water and freed from residues of water by heating in vacuo up to a final temperature of 80°.

After dilution of the batch with water, it is also possible for the mixture to be extracted by shaking with methylene chloride and the organic phase to be washed several times with water and dried over sodium sulphate. After removal of the methylene chloride by distillation, finally in vacuo up to 80°, an oil is likewise obtained as the distillation residue as above.

The resulting product has the formula

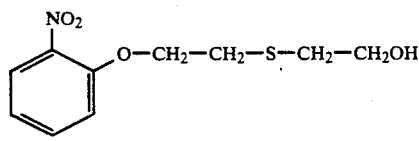

$^1$H-NMR in D$_6$-DMSO (TMS as the internal standard).

| | |
|---|---|
| $\delta$ = 2.66 ppm | (2H, t) |
| $\delta$ = 2.90 ppm | (2H, t) |
| $\delta$ = 3.53–3.60 ppm | (2H, q) |
| $\delta$ = 4.28 ppm | (2H, t) |
| $\delta$ = 4.78 ppm | (1H, t) |
| $\delta$ = 7.04–7.11 ppm | (1H, m) |
| $\delta$ = 7.31–7.34 ppm | (1H, d?) |
| $\delta$ = 7.55–7.63 ppm | (1H, m) |
| $\delta$ = 7.78–7.83 ppm | (1H, m) |

150 g of the oil of the formula last given are emulsified in 1,000 ml of water by stirring. 7.2 g of sodium acetate are added, the pH is brought to 5.2 with acetic acid and a catalyst solution of 1.2 g of tungstic acid which has been prepared in the manner described in Example 13 is added.

111 ml of 35% strength hydrogen peroxide are added dropwise at 55°-60° in the course of one hour, cooling noticeably being necessary during the first half. The temperature is then kept at 60° for 2 hours, 25 ml of 35% strength hydrogen peroxide are subsequently added if necessary and the temperature is maintained for a further 2 hours. When the oxidation has ended, the resulting oilwater mixture is cooled to 0°-5°, whereupon crystallization starts, if appropriate after seeding. The resulting product is filtered off with suction, comminuted in 1,000 ml of ice-water using a high-speed stirrer, filtered off with suction and washed with 500 ml of icewater. The product corresponds to the formula

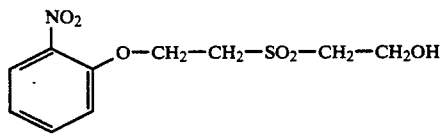

Melting point: 74°-76° (crude product).

$^1$-NMR in D$_6$-DMSO (TMS as the internal standard).

| | |
|---|---|
| $\delta$ = 3.36 ppm | (2H, t) |
| $\delta$ = 3.69 ppm | (2H, t) |
| $\delta$ = 3.80–3.88 ppm | (2H, m) |
| $\delta$ = 4.54 ppm | (2H, t) |
| $\delta$ = 5.14 ppm | (1H, t) |
| $\delta$ = 7.14 ppm | (1H, t?) |
| $\delta$ = 7.39–7.42 ppm | (1H, d?) |
| $\delta$ = 7.62–7.68 ppm | (1H, t?) |

| | |
|---|---|
| δ = 7.85-7.88 ppm | (1H, d?) |

80.0 g of the resulting o-nitro compound are heated to 60° in 600 ml of methanol in the presence of 6 g of Raney nickel under a hydrogen pressure of 10 bar in the course of one hour. A hydrogen pressure of 10 bar is maintained continuously, until the consumption has stopped. After cooling and letting down, the Raney nickel is removed from the resulting solution by filtration and the solution is then evaporated. A crystalline product of the formula

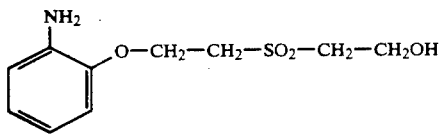

is obtained.

A sample recrystallized from 10 volumes of isopropanol shows a melting point of 79°-81°.

$^1$-NMR in D$_6$-DMSO (TMS as the internal standard).

| | |
|---|---|
| δ = 3.32 ppm | (2H, t) |
| δ = 3.61 ppm | (2H, t) |
| δ = 3.78-3.84 ppm | (2H, q) |
| δ = 4.26 ppm | (2H, t) |
| δ = 4.75 ppm | (2H, s) |
| δ = 5.19 ppm | (1H, t) |
| δ = 6.42-6.49 ppm | (1H, m) |
| δ = 6.57-6.70 ppm | (2H, m) |
| δ = 6.76-6.81 ppm | (1H, dd) |

EXAMPLE 16

50 g of the o-amino compound of the formula

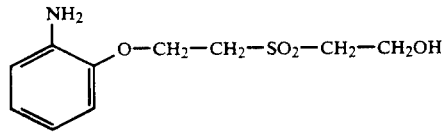

are introduced into 125 ml of 96% strength sulphuric acid at 0°-5°. The batch is stirred for some hours at 0°-5° until only traces of the educt are still present and a chromatographic sample no longer shows any change in the reaction mixture with respect to time. The batch is stirred into 900 g of ice, after which the reaction product precipitates as crystals. The precipitate is filtered off with suction at 0°-5° and washed free from sulphate with isopropanol or 25% strength sodium chloride solution. The resulting product of the formula

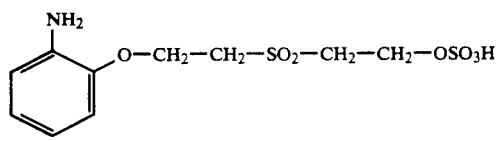

is dried in vacuo at 50°-60°.

$^1$H-NMR in D$_6$-DMSO (TMS as the internal standard).

| | |
|---|---|
| δ = 3.54 ppm | (2H, t) |
| δ = 3.67 ppm | (2H, t) |
| δ = 4.15 ppm | (2H, t) |
| δ = 4.44 ppm | (2H, t) |
| δ = 6.94-7.04 ppm | (1H, m) |
| δ = 7.22-7.37 ppm | (3H, m) |

EXAMPLE 17

40.0 g of the amino compound of Example 3, of the formula

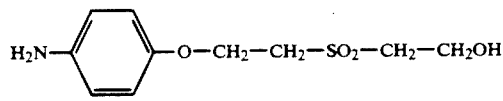

are introduced into 120 ml of 20% strength oleum at 15°-20°. The mixture is subsequently stirred at 20° for a further hour until complete sulphation of the nucleus has occurred and a sample no longer shows the product of Example 6 (only sulphation of the hydroxyl group). The reaction mixture is stirred into 200 g of ice and the solution is diluted with 200 g of water.

220 g of calcium carbonate are introduced into the solution at below 10° until the pH reaches 4.5, the calcium sulphate which has precipitated is filtered off with suction and the filtercake is washed free from the amino compound with about 500 ml of water. The resulting filtrate contains the very readily soluble compound of the formula

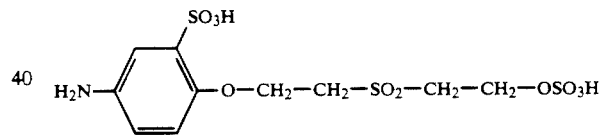

If appropriate after evaporation in vacuo to the desired volume, the filtrate can be reacted directly, as has been described at the end of Example 2.

If the filtrate is evaporated to dryness, a viscous hydroscopic mass which becomes brittle and pulverizable only after drying at a high temperature in vacuo over sodium hydroxide is obtained.

$^1$H-NMR in D$_2$O-D$_2$SO$_4$ (trimethylsilylpropanesulphonic acid, Na salt as the internal standard, 250 MHz apparatus).

| | |
|---|---|
| δ = 3.83 ppm | (2H, t) |
| δ = 3.90 ppm | (2H, t) |
| δ = 4.45 ppm | (2H, t) |
| δ = 4.62 ppm | (2H, t) |
| δ = 7.23-7.26 ppm | (1H, d, J$_{ortho}$ ≈ 8 Hz) |
| δ = 7.52-7.55 ppm | (1H, dd, J$_{ortho}$ ≈ 8 Hz, J$_{meta}$ ≈ 2 Hz) |
| δ = 7.78 ppm | (1H, d, J$_{meta}$ 2 Hz) |

EXAMPLE 18

70.0 g of the amino compound of Example 15, of the formula

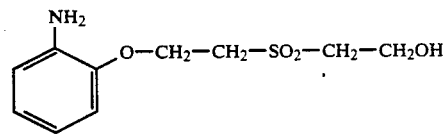

are introduced into 210 ml of 20% strength oleum at 20°-25° with gentle external cooling. After the solution has been stirred for three hours, it is introduced into 1,600 g of ice. The mixture is diluted with 1,000 ml of water and about 395 g of calcium carbonate are then introduced at below 10°, until a pH of 5.0 is reached. The calcium sulphate is filtered off with suction and washed with water until the precipitate is free from aromatic amino compound. After the filtrates have been evaporated in vacuo, the compound of the formula

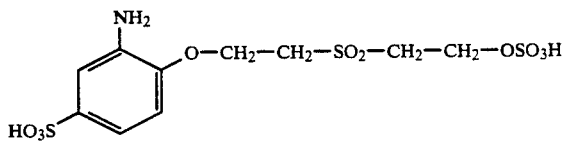

is obtained as the readily water-soluble calcium salt in the form of a readily drying white residue.

$^1$H-NMR in $D_2O$-$D_2SO_4$ (trimethylsilylpropanesulphonic acid, Na salt as the internal standard, 250 MHz apparatus).

| | |
|---|---|
| δ = 3.74 ppm | (2H, t) |
| δ = 3.88 ppm | (2H, t) |
| δ = 4.49 ppm | (2H, t) |
| δ = 4.72 ppm | (2H, t) |
| δ = 7.30–7.34 ppm | (1H, d, $J_{ortho} \approx$ 10 Hz) |
| δ = 7.79 ppm | (1H, d, $J_{meta} \approx$ 2 Hz) |
| δ = 7.83–7.87 ppm | (1H, dd, $J_{ortho} \approx$ 10 Hz, $J_{meta} \approx$ 2 Hz) |

EXAMPLE 19

50.0 g of the oil obtained in Example 13, of the formula

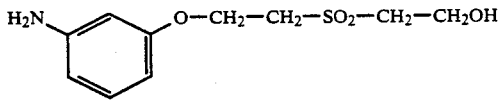

are introduced into 150 ml of 30% strength oleum at 15°-20°. The mixture is stirred overnight. When a chromatographic sample indicates the disappearance of the isomeric nuclear-monosulphonic acid mixture and a uniform nuclear-disulphonic acid has formed, the batch is introduced into 1,200 g of ice, the resulting solution is diluted with 1,000 ml of water and about 270 g of calcium carbonate are introduced at below 10°, until a pH of 5.0 is established in the mixture.

The calcium sulphate is separated off by filtration and washed free from aromatic aminosulphonic acid with water and the filtrates are evaporated in vacuo. After drying in vacuo at 40° over sodium hydroxide, the calcium salt of the compound

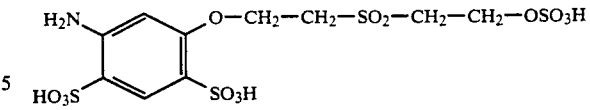

is obtained as a highly hydroscopic powder which deliquesces in air.

$^1$H-NMR in $D_2O$-$D_2SO_4$ (trimethylsilylpropanesulphonic acid, Na salt as the internal standard).

| | |
|---|---|
| δ = 3.84 ppm | (2H, t not resolved) |
| δ = 3.91 ppm | (2H, t not resolved) |
| δ = 4.47 ppm | (2H, t not resolved) |
| δ = 4.59 ppm | (2H, t not resolved) |
| δ = 6.77 ppm | (1H, s) |
| δ = 8.08 ppm | (1H, s) |

EXAMPLE 20

40.0 g of 1-acetylamino-4-(2-chloroethoxy)-benzene are boiled with 19.0 g of 2-mercaptoethanol and 12.8 g of powdered potassium hydroxide in 150 ml of ethanol until a chromatographic sample indicates complete replacement of the chlorine atom in the educt by the β-hydroxyethylmercaptide radical.

The resulting suspension is diluted with 300 ml of water and a neutralized solution of 0.5 g of tungstic acid in 10 ml of water and 2.0 g of sodium acetate is added to the mixture. The pH is then brought to 5.5 with acetic acid.

To oxidize the sulphide, 49 ml of 35% strength hydrogen peroxide are added dropwise at 50°-60° in the course of one hour and the temperature is then kept at 60° for about a further 3 hours, until the oxidation of the sulphoxide formed as the intermediate product to the sulphone is complete.

After the ethanol has been distilled off in vacuo, the sulphone formed of the formula

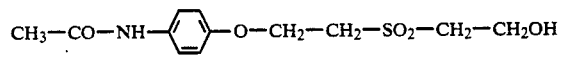

is isolated by filtration.

Melting point: 107°–108° C.

$^1$H-NMR in $D_6$-DMSO (TMS as the internal standard).

| | |
|---|---|
| δ = 2.02 ppm | (3H, s) |
| δ = 3.32 ppm | (2H, t) |
| δ = 3.62 ppm | (2H, t) |
| δ = 3.84 ppm | (2H, m) |
| δ = 4.32 ppm | (2H, t) |
| δ = 5.16 ppm | (1H, s) |
| δ = 6.92 ppm | (2H, d) |
| δ = 7.50 ppm | (2H, d) |
| δ = 9.81 ppm | (1H, s) |

Boiling of the product in 10 volumes of 10% strength hydrochloric acid, cooling of the resulting solution, neutralization with sodium hydroxide solution and filtration of the precipitate with suction gives the same amino compound as in Example 3 or 4.

EXAMPLE 21

40.0 g of the oil obtained in Example 13, of the formula

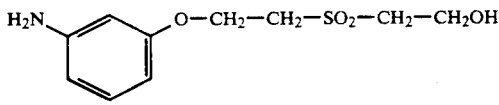

are introduced into a mixture of 50 ml of 20% strength oleum and 50 ml of 96% strength sulphuric acid at 0°–10°. A further 50 ml of 20% strength oleum are then added to the reaction mixture and the temperature is subsequently kept at 20°–22° for about 5 hours until a chromatographic sample indicates complete monosulphonation in the aromatic nucleus. The batch is stirred into 1,250 g of ice and the resulting solution is diluted with 1,000 ml of water.

The sulphuric acid is neutralized by slow introduction of about 270 g of calcium carbonate until the pH is 5.0, the calcium sulphate is filtered off and washed with water until the filtercake is freed from diazotizable material and the combined filtrates are evaporated to dryness in vacuo. The calcium salts of a mixture of the position-isomer sulphonic acids of the formulae

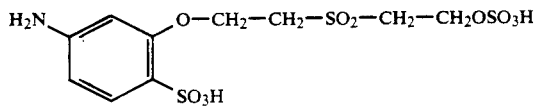

and

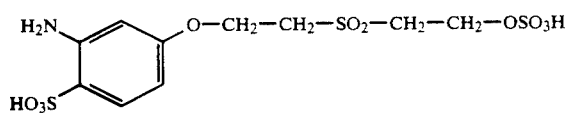

are obtained.

$^1$H-NMR of the isomer mixture in $D_2O$-$D_2SO_4$. (trimethylsilylpropanesulphonic acid, Na salt as the internal standard).

| | |
|---|---|
| δ = 3.76–3.93 ppm | (4H, 4 bands) |
| δ = 4.50–4.66 ppm | (4H, 4 bands) |
| δ = 7.14–7.23 ppm | (2H, 3 bands) |
| δ = 7.85–7.92 ppm | (1H, 3 bands) |

EXAMPLE 22

275 g of 4-nitro-2-hydroxy-toluene are dissolved in 2,500 ml of water with 260 ml of 2N sodium hydroxide solution at pH 8.5 and 80°. 145 g of 2-chloroethanol are allowed to run in and the pH in the reaction mixture is maintained further at 8.5 and the temperature at 80°. Under the same conditions, a further 65 g of 2-chloroethanol are added after 3 hours and four further portions of 65 g each of 2-chloroethanol are subsequently added at intervals of in each case 2 hours, until the educt is no longer detectable by chromatography. After cooling, while stirring, the resulting emulsion gives coarse rectangular crystals, which are filtered off with suction, washed with 2 l of water and dried in vacuo. Yield 344 g. Melting point 103°–104°.

343 g of the resulting product are introduced into 1,000 ml of thionyl chloride in the course of 30 minutes. When the evolution of gas has subsided, 10 ml of thionyl chloride are added and the mixture is heated to the reflux point in the course of about 15 minutes. It is boiled under reflux for 2 hours, and when the reaction has ended the solution is cooled to room temperature and introduced into 9.5 kg of ice. The product which has precipitated is filtered off with suction, washed with 7 l of water and, after homogenizing using a high-speed stirrer, washed again with water until the runnings are neutral. After drying in vacuo at room temperature, 373 g of a product of the formula

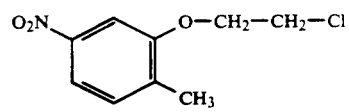

with a melting point of 65° are obtained.

373 g of the resulting 2-β-chloroethoxy-4-nitrotoluene are heated at 70° in 1,600 ml of acetonitrile with 274 g of potassium carbonate and 149 g of 2-mercaptoethanol under a nitrogen atmosphere. After 7 hours, 37 g of potassium carbonate and 37 g of 2-mercaptoethanol are subsequently added and this procedure is repeated after a further 4 hours. When the reaction has ended, the batch is poured into 6.2 l of water. An oil can be separated off from the resulting emulsion, after settling, and the aqueous phase can be extracted with methylene chloride. Combining of the extract and the oil separated off, washing of the resulting solution with water, drying over sodium sulphate and removal of the methylene chloride by distillation, finally in vacuo at 70° under 18 mbar, gives 440 g of an oil of the formula

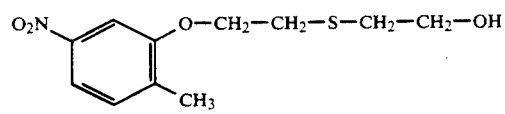

$^1$H-NMR in $D_6$-DMSO (TMS as the internal standard).

| | |
|---|---|
| δ = 2.28 ppm | (3H, s) |
| δ = 2.72 ppm | (2H, t) |
| δ = 2.98 ppm | (2H, t) |
| δ = 3.53–3.63 ppm | (2H, m) |
| δ = 4.28 ppm | (2H, t) |
| δ = 4.81 ppm | (1H, t) |
| δ = 7.42–7.47 ppm | (1H, d) |
| δ = 7.71 ppm | (1H, d; weak splitting) |
| δ = 7.72–7.78 ppm | (1H, dd) |

To oxidize the thioether obtained above, either the crude emulsion obtained above after pouring into water, bypassing the ethylene chloride extraction described, or the oil obtained after extraction is employed, the procedure being analogous in both cases. In the latter case, 440 g of the thioether are emulsified in 3.8 l of water, 23 g of sodium acetate are added, the pH is brought to 5.8 with 7.6 ml of ice-water and a catalyst solution of 3.5 g of tungstic acid, which is prepared in accordance with the instructions in Example 13, is added. 300 ml of 35% strength hydrogen peroxide are now added dropwise at 55°–60° in the course of one hour, with occasional cooling, and the temperature is then kept at 60°. After 5 hours, a further 120 ml of hydrogen peroxide are subsequently added. When the oxidation has ended after about a further 4 hours at 60°, the resulting emulsion is stirred until cold and if appropriate seeded. The resulting crystal mass is filtered off with suction, washed with ice-cold water and dried at 50° in vacuo. The product of the formula (445 g, melting point 76°–78°, crude)

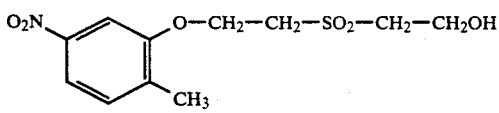

shows the following nuclear magnetic resonance spectrum:

¹H-NMR in D₆-DMSO (TMS as the internal standard).

| | |
|---|---|
| δ = 2.28 ppm | (3H, s) |
| δ = 3.36 ppm | (2H, t) |
| δ = 3.63 ppm | (2H, t) |
| δ = 3.83–3.92 ppm | (2H, m) |
| δ = 4.54 ppm | (2H, t) |
| δ = 5.18 ppm | (1H, t) |
| δ = 7.42–7.47 ppm | (1H, d) |
| δ = 7.80–7.84 ppm | (2H, m) |

400 g of the resulting nitro compound are hydrogenated in 1,800 ml of methanol, after addition of 20 g of Raney nickel, in an autoclave under a hydrogen pressure of 10 bar at 55°–60°. The resulting solution is clarified at 60° to remove the Raney nickel and the filtrate is evaporated in a rotary evaporator under reduced pressure. The amine of the formula

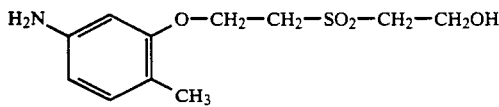

which has a melting point of 99°–102°, is obtained as the residue.

¹H-NMR, in D₆-DMSO (TMS as the internal standard).

| | |
|---|---|
| δ = 1.98 ppm | (3H, s) |
| δ = 3.32 ppm | (2H, t) |
| δ = 3.60 ppm | (2H, t) |
| δ = 3.78–3.84 ppm | (2H, m) |
| δ = 4.19 ppm | (2H, t) |
| δ = 4.84 ppm | (2H, broad) |
| δ = 5.14 ppm | (1H, t) |
| δ = 6.03–6.07 ppm | (1H, dd) |
| δ = 6.19 ppm | (1H, d) |
| δ = 6.69–6.73 ppm | (1H, d) |

EXAMPLE 23

If 100 g of the amino compound of Example 22 are introduced into 250 ml of 96% strength sulphuric acid at 0°, the mixture is stirred at this temperature for 17 hours, the resulting solution is introduced into 400 g of ice and the crystals which have precipitated after a few hours are filtered off with suction and washed free from sulphuric acid with isopropanol, the sulphuric acid half-ester of the formula

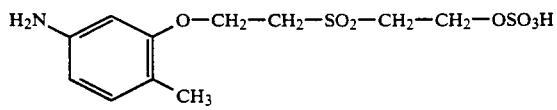

is obtained.

It shows the following nuclear magnetic resonance spectrum:

¹H-NMR in D₆-DMSO (TMS as the internal standard).

| | |
|---|---|
| δ = 2.15 ppm | (3H, s) |
| δ = 3.50 ppm | (2H, t) |
| δ = 3.66 ppm | (2H, t) |
| δ = 4.12 ppm | (2H, t) |
| δ = 4.36 ppm | (2H, t) |
| δ = 6.82–6.85 ppm | (1H, dd) |
| δ = 7.93 ppm | (1H, d) |
| δ = 7.21–7.24 ppm | (1H, d) |

EXAMPLE 24

100 g of the amino compound of Example 22 are gradually introduced into 300 ml of 20% strength oleum. The mixture is subsequently stirred at 20° for 5 hours until everything has dissolved. The resulting solution is introduced into 1,200 g of ice, the solution is neutralized to pH 5.5 with about 580 g of calcium carbonate and the gypsum which has precipitated is filtered off and washed free from the aminosulphonic acid with water. The filtrates are evaporated to dryness in vacuo. The resulting product is the calcium salt of a sulphonic acid of the formula

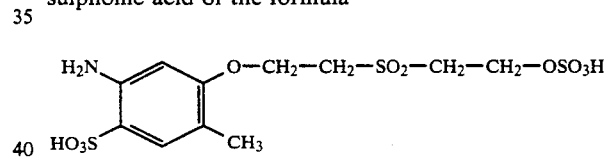

¹H-NMR in D₂O+D₂SO₄ (trimethylsilylpropanesulphonic acid, Na salt as internal standard).

| | |
|---|---|
| δ = 2.18 ppm | (3H, s) |
| δ = 3.73 ppm | (2H, t blurred) |
| δ = 3.82 ppm | (2H, t blurred) |
| δ = 4.47–4.53 ppm | (4H, several coincident bands) |
| δ = 6.97 ppm | (1H, s) |
| δ = 7.59 ppm | (1H, s) |

I claim:

1. A triphendioxazine reactive dyestuff of the formula

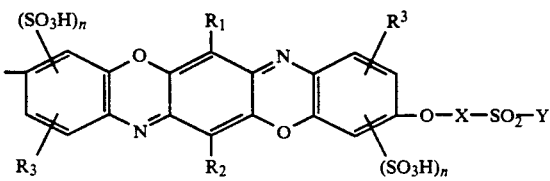

wherein x denotes an aliphatic bridge member selected from the group comprising 1,3- or 1,2-propylene, 1,4-, 1,3- or 2,3-butylene, 1,5-pentylene, 1,6-hexylene, 2,2-dimethyl-1,3-propylene, 2-ethyl-1,3-propylene, 1,4-, 1,3-cyclohexylene, 2-hydroxy-1,3-propylene, 2-oxo-1,3-propylene, 2-sulphato-1,3-propylene, —CH₂—CH₂—O—CH₂—CH₂—, —(CH₂—CH₂—O)₂₋₃—CH₂—CH₂—

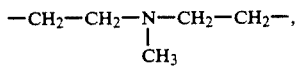

—CH₂—CH₂—NH—CH₂—CH₂—,

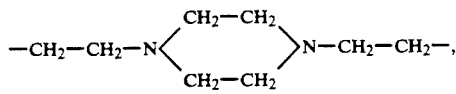

—CH₂—CH₂—CO—NH—CH₂—CH₂—, —CH₂—CO—NH—CH₂—CH₂—, —CH₂—CH₂—NH—CO—CH₂—, and —CH₂—CH₂—NH—CO—CH₂—CH₂—, Y denotes —CH=CH₂ or —CH₂—CH₂—Z, wherein denotes OSO₃H, S₂O₃H, Cl, Br, O—COCH₃, OPO₃H₂ or N(R₄)₃ where R₄=C₁-C₄-alkyl, n denotes 0-2, R₁ and R₂ denote Cl, and R₃ denotes H.

2. A dyestuff of claim 1 of the formula

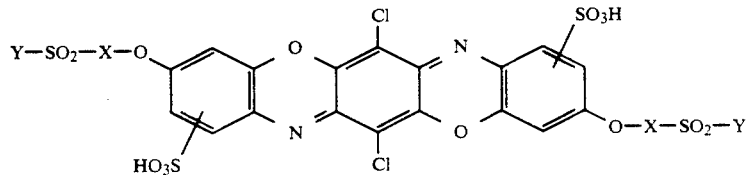

3. A dyestuff of claim 1 of

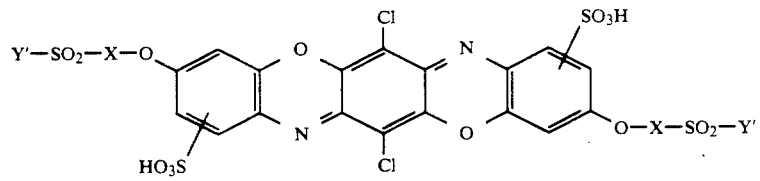

wherein x denotes 1,3- or 1,2-propylene and 1,4-, 1,3- or 2,3-butylene

Y₁ denotes CH₂—CH₂—OSO₃H or —CH=CH₂.

4. A dyestuff of claim 1, wherein Z denotes OSO₃H.

5. A dyestuff of claim 1, wherein n denotes O.

6. A dyestuff of claim 1, of the formula

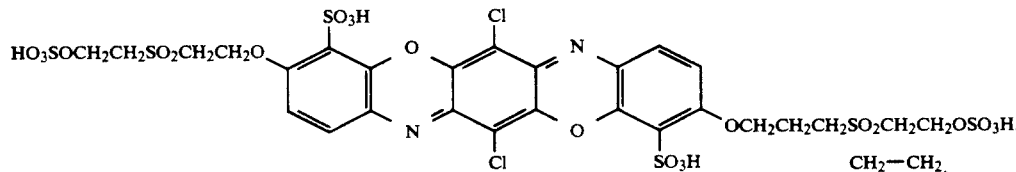

7. An amine of the formulae

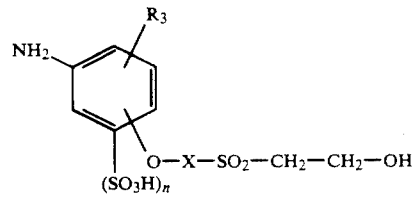

and

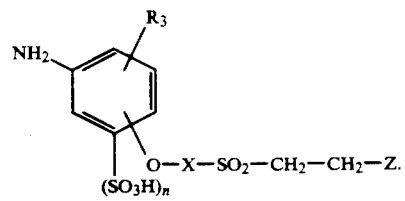

wherein

X denotes an aliphatic bridge member, selected from the group comprising 1,3- or 1,2-propylene, 1,4-, 1,3- or 2,3-butylene, 1,5-pentylene, 1,6-hexylene, 2,2-dimethyl-1,3-propylene, 2-ethyl-1,3-propylene, 1,4-, 1,3-cyclohexylene, 2-hydroxy-1,3-propylene, 2-oxo-1,3-propylene, 2-sulphato-1,3-propylene, —CH₂—Ch₂—O—CH₂—CH₂—,—(CH₂—CH₂—O)₂₋₃—CH₂—CH₂—,

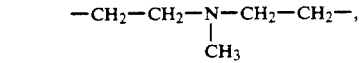

—CH₂—CH₂—NH—CH₂—CH₂—,

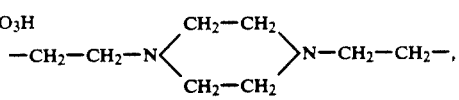

—CH₂—CH₂—CO—NH—CH₂—CH₂—, —CH₂—CO—NH—CH₂—CH₂—, —CH₂—CH₂—NH—CO—CH₂—, and —CH₂—CH₂—NH—CO—CH₂—CH₂—.

z denotes OSO₃H, S₂O₃H, Cl, Br, O—COCH₃, OPO₃H₂ or N⊕(R₄)₃ where R₄=C₁-C₄-alkyl, n denotes 0-2, R₃ denotes H.

* * * * *